United States Patent
He et al.

(10) Patent No.: US 6,171,866 B1
(45) Date of Patent: Jan. 9, 2001

(54) LUMINESCENCE INDICATOR FOR DETERMINING CALCIUM IONS

(75) Inventors: Huarui He, Alpharetta; Mark Alan Mortellaro, Woodstock, both of GA (US)

(73) Assignee: AVL Medical Instruments, Schaffhausen (CH)

(*) Notice: Under 35 U.S.C. 154(b), the term of this patent shall be extended for 0 days.

(21) Appl. No.: 09/164,516

(22) Filed: Sep. 30, 1998

(51) Int. Cl.$^7$ .................................................. G01N 33/20
(52) U.S. Cl. ............................ 436/79; 422/56; 422/82.05; 422/82.06; 422/82.07; 422/82.08; 422/82.09; 436/73; 436/172; 562/405; 562/433; 562/443
(58) Field of Search ............................... 436/73, 79, 172; 422/82.05–82.09, 56; 562/443, 433, 405

(56) References Cited

U.S. PATENT DOCUMENTS

| | | |
|---|---|---|
| 4,603,209 | 7/1986 | Tsien et al. . |
| 5,049,673 | 9/1991 | Tsien et al. . |
| 5,516,911 | 5/1996 | London et al. . |
| 5,723,340 * | 3/1998 | Karpf ..................................... 436/79 |

FOREIGN PATENT DOCUMENTS

| | | |
|---|---|---|
| 5-165159 * | 6/1993 | (JP) . |
| 9-124566 * | 5/1997 | (JP) . |
| 96/16327 | 5/1996 | (WO) . |

OTHER PUBLICATIONS

H. He et al. Anal. Chem., 65, 123–127, Jan. 1993.*
Topics in Fluorescence Spectroscopy, Probe Design and Chemical Sensing, vol. 4, pp. 133–134.

* cited by examiner

Primary Examiner—Arlen Soderquist
(74) Attorney, Agent, or Firm—Baker Botts, L.L.P.

(57) ABSTRACT

The invention relates to a compound having the general Formula I:

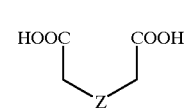

(I)

including its salts, where Z is either the group having the general Formula II:

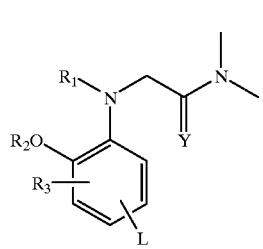

(II)

where $R_1$ is alkyl having 1–4 C atoms, alkoxyalkyl having 2–5 C atoms or aryloxyalkyl whose alkyl group has 1–4 C atoms, $R_2$ is alkyl having 1–4 C atoms or alkoxyalkyl having 2–5 C atoms, $R_3$ is H, alkoxy having 1–4 C atoms, halogen, NO or $NO_2$, Y is $H_2$ or O and L is a luminophoric moiety in a position para or meta to the nitrogen,

X1    X2    X3    X4

X5    X6    X7    X8

X9 or is the group having the general Formula III:

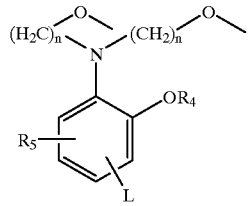
(III)

where n is 2 or 3, $R_4$ is alkyl having 1–4 C atoms or alkoxyalkyl having 2–5 C atoms, $R_5$ is H, alkoxy having 1–4 C atoms, halogen, NO or $NO_2$ and L is a luminophoric moiety in a position para or meta to the nitrogen, or is the group having the general Formula IV:

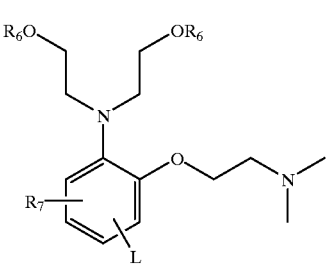
(IV)

where $R_6$ is alkyl having 1–3 C atoms or phenyl, $R_7$ is H, alkoxy having 1–4 C atoms, halogen, NO or $NO_2$ and L is a luminophoric moiety in a position para or meta to the nitrogen.

The compound of the invention can be used as a luminescence indicator for the determination of calcium ions in a sample.

38 Claims, 10 Drawing Sheets

LUMINESCENCE INDICATOR FOR DETERMINING CALCIUM IONS

The present invention relates to luminescence indicators for determining ionized calcium in a sample as well as optical sensors comprising these luminescence indicators. The invention also relates to a method of determining calcium ions in a sample using the luminescence indicators of the invention.

BACKGROUND OF THE INVENTION

For determining the calcium ions, the sample is contacted at least indirectly with a luminescence indicator (=luminophore-ionophore) having a luminophoric moiety and an ionophoric moiety, which ionophoric moiety reacts with the calcium ions present in the sample, whereupon the luminescence of the luminophoric moiety is measured and the concentration or the activity of the ionized calcium is deduced utilizing the test reading, i.e. the calcium ion is determined.

A determination method of this type is based on the reversible binding of calcium ions to a $Ca^{2+}$-selective ionophore and on the so-called "PET effect" between the ionophore and a luminophoric moiety.

The reversible binding of calcium ions to the ionophore proceeds according to the principle of mass action (Equation 1):

$$ICa^{2+} \overset{Kd}{\longleftrightarrow} I + Ca^{2+} \qquad (1)$$

wherein, at a given ionic strength and temperature, the dissociation constant ($K_d$) is given by Equation 2, $$K_d = \frac{cI \cdot cCa^{2+}}{cICa^{2+}} \qquad (2)$$

wherein I means the ionophore with the charge number –2, ICa the ionophore-ion complex and c the concentration. In the following, $K_d$ and $cCa^{2+}$ are given in mol/l and mmol/l, respectively.

The $PK_d$ value (Equation 3) is the negative common logarithm of the dissociation constant:

$$PK_d = -\log(K_d) \qquad (3)$$

The term "PET effect" denotes the transfer, induced by photons, of electrons (photoinduced electron transfer=PET) from the ionophoric moiety or ionophore to the luminophoric moiety or luminophore, which causes a decrease in the (relative) luminescence intensity and the luminescence decay time of the luminophore. Absorption and emission wavelengths of the luminophoric moiety or luminophore, respectively, remain basically unaffected in the process (J. R. Lakowicz in "Topics in Fluorescence Spectroscopy", Volume 4: Probe Design and Chemical Sensing; Plenum Press, New York & London (1994)).

By the binding of ions to the ionophore, the PET effect is reduced or completely suppressed, so that there is an increase in the luminescence of the luminophoric moiety. Hence, the concentration or the activity of the ion to be determined can be deduced by measuring the change in luminescence properties, i.e. luminescence intensity and/or luminescence decay time.

In mammals, calcium plays important physiological roles. These roles include: (1) controlling blood coagulation by activating the formation of thrombin from prothrombin, (2) excitation of muscle, heart and nerve cells, including acting as a second messenger like cAMP.

Measurement of extracellular ionized calcium is an essential part of medical diagnostics. The measurement of ionized calcium, blood gases and potassium is mandatory to allow for the maintenance of good cardiac function during liver transplant operations or other operations that require bypassing the heart and lung functions and using artificial life support.

Ion selective electrodes (ISE) have been used for determining calcium ions in body fluids for many years. Serious drawbacks of electrochemical measuring arrangements are the requirement of a reference element, sensitivity towards electrical potentials and electromagnetic interference. While ion-selective electrodes are rugged and reliable, they are expensive to use in a disposable device application. In addition, these electrodes require an electrical connection of the sample measurement device to the instrument.

However, optical methods or optical sensors do not require a reference element. The optical signals are independent of external potentials and currents. Such optical methods of determining calcium as are known to date are based f.i on the measurement of the luminescence intensity or luminescence decay time of a calcium-specific luminescence indicator or the light absorption of a calcium-specific absorption indicator, which depend directly or indirectly on the concentration or activity of calcium ions.

In order to determine intracellular calcium concentrations, indicators which change their absorption and/or luminescence properties by reversible binding of calcium ions (see above, Equation 1) are, e.g., used. Suitable indicators for intracellular calcium determination are based e.g. on tetracarboxylate $Ca^{2+}$ chelating compounds having the octacoordinate ligating group characteristics of EGTA (=ethylene glycol bis(-beta-aminoethyl ether)-N,N,N',N'-tetraacetic acid) and BAPTA (=1,2-bis(2-aminophenoxy)ethane N,N,N',N'-tetraacetic acid).

U.S. Pat. No. 4,603,209 e.g. discloses the BAPTA analogs which are electronically coupled to one or two fluorescent dye molecules capable of being excited in the UV range. By the binding of calcium ions to the ionophore, the absorption wavelength of the dye (a stilbene derivative) is changed. By means of suitable electron-withdrawing or electron-donating substituents it is feasible to change the calcium dissociation constant in the range of 80 to 250 nmol/l.

U.S. Pat. No. 5,049,673 further describes BAPTA analogs which—in electronically decoupled condition—are bound to xanthene dyes (fluoresceines, rhodamines). As a result of the electronic decoupling from the fluorophore, a PET effect occurs which is recognizable from the constant spectral position of the fluorescence emission band and the increasing fluorescence intensity depending on increasing concentrations of $Ca^{2+}$ (see FIG. 4a of the reference). From the low $K_d$ values it can be seen that the fluoroionophores described (see FIG. 6 of the reference) are not useful for the determination of millimolar concentrations of $Ca^{2+}$ in whole blood or blood plasma.

As a consequence of the very low dissociation constant, such calcium-ionophores are useful for determining $Ca^{2+}$ in samples having correspondingly low calcium values, such as e.g. intracellular $Ca^{2+}$. In contrast to this, blood plasma for example has $Ca^{2+}$ concentrations in the range of about 0.4–2 mmol/l. Suitable ionophores for optical determination of $Ca^{2+}$ in the blood or blood plasma thus must have correspondingly high $K_d$ values. Ideal $K_d$ values lie within the expected range of the $Ca^{2+}$ concentrations or activities to be determined.

From U.S. Pat. No. 5,516,911, fluorescent indicators based on fluorinated BAPTA derivatives are known which have $K_d$ values in the millimolar range. One major disadvantage with this method is the very complicated synthesis of fluorinated BAPTA derivatives.

Moreover, the known ionophores based on BAPTA or on derivatives thereof in an aqueous environment and at normal ambient temperatures are not particularly stable chemically (see U.S. Pat. No. 4,603,209, column 26, lines 40–46). This is particularly disadvantageous in determination procedures using optical sensors in measuring situations requiring a high shelf life (durability) of the sensor or where, for monitoring purposes, one sensor is to be used for measuring over prolonged time periods.

The present invention aims at avoiding these disadvantages and problems and has as its object to provide luminophore-ionophores for the optical determination of calcium ions, whose ionophores if compared to such BAPTA compounds as are known to date, in particular fluorinated derivatives, are more easily synthesizable and—in electronically decoupled condition—can be covalently bound to suitable luminophores.

Further, the ionophores of the provided luminophore-ionophores are to exhibit $K_d$ values allowing the determination of physiological calcium values without requiring previous diluting of the sample material, wherein, by means of suitable substituents, the $K_d$ values are to be adjustable with regard to the expected values of the concentrations of $Ca^{2+}$ in the sample material which are to be determined.

In addition, it is to be possible for the luminophore-ionophores to be bound to a hydrophilic polymer material by means of a chemical group in order to use them in optical sensors.

Preferred luminophore-ionophores should not exhibit inherent pH dependence in the expected pH range of the sample and should be excitable by light of commercially available LEDs (preferably >420 nm). These luminophore-ionophores should, in addition, be chemically stable in an aqueous environment even at high ambient temperatures and over prolonged time periods (>3 months).

SUMMARY OF THE INVENTION

The present object is achieved in that a compound having the general Formula I:

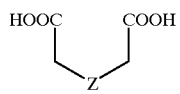

(I)

including its salts is provided, where Z is either the group having the general Formula II:

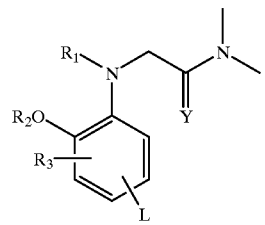

(II)

where $R_1$ is alkyl having 1–4 C atoms, alkoxyalkyl having 2–5 C atoms or aryloxyalkyl whose alkyl group has 1–4 C atoms, $R_2$ is alkyl having 1–4 C atoms or alkoxyalkyl having 2–5 C atoms, $R_3$ is H, alkoxy having 1–4 C atoms, halogen, NO or $NO_2$, Y is $H_2$ or O and L is a luminophoric moiety in a position para or meta to the nitrogen, or is the group having the general Formula III:

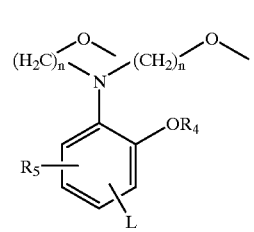

(III)

where n is 2 or 3, $R_4$ is alkyl having 1–4 C atoms or alkoxyalkyl having 2–5 C atoms, $R_5$ is H, alkoxy having 1–4 C atoms, halogen, NO or $NO_2$ and L is a luminophoric moiety in a position para or meta to the nitrogen, or is the group having the general Formula IV:

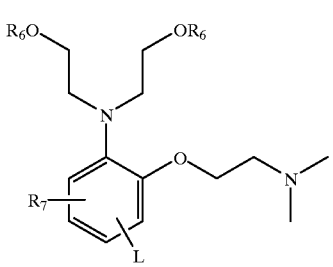

(IV)

where $R_6$ is alkyl having 1–3 C atoms or phenyl, $R_7$ is H, alkoxy having 1–4 C atoms, halogen, NO or $NO_2$ and L is a luminophoric moiety in a position para or meta to the nitrogen.

Thus, the compounds of the invention have the following general formulae:

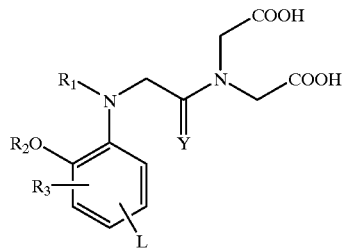

-continued

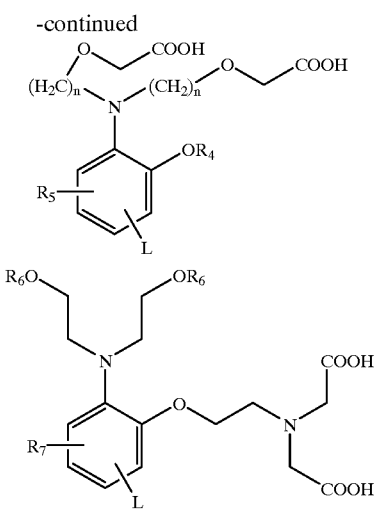

where $R_1$, $R_2$, $R_3$, $R_4$, $R_5$, $R_6$, $R_7$, Y, L and n have the meaning indicated above. The ionophores of the compounds of the invention are based on the basic structure of the o-anisidine with a diacetate group and can be synthesized in a simple manner (see below).

The $K_d$ values of the ionophores of the invention lie within a range that makes them useful in particular for the determination of physiological concentrations of $Ca^{2+}$ (see examples shown in Table 1: $K_d$=0.2–123 mmol/l $Ca^{2+}$). The $K_d$ values can be adjusted by means of suitable substituents (see below).

Due to the aliphatically bound nitrogen of the imino-N, N-diacetate ligand portion the ionophores of the invention having a group of the general Formula II exhibit an inherent pH-dependence at a neutral pH and are not stable in an aqueous environment over a prolonged time period. Basically, however, these ionophores are applicable for any measuring situation in which the pH of the sample is known or can be adjusted to a known value by means of a pH buffer and if there is no need for a prolonged useful life in an aqueous environment.

In the compounds of the invention having a group of the general Formula II, $R_1$ is preferably alkyl having 4 C atoms, alkoxyalkyl having 3–4 C atoms or aryloxyalkyl whose alkyl group has 2 C atoms. $R_2$ is preferably alkyl having 1–4 C atoms, more preferably methyl. $R_3$ is advantageously located in a position para to the oxygen of the o-anisidine and is preferably H or methoxy.

The particularly advantageous ionophores of the compounds having a group of the general Formula III do not exhibit an inherent pH-dependence at physiological pH values (presumably even alkaline ones) and in an aqueous environment at normal ambient temperature are chemically stable even over prolonged time periods. These ionophores are likewise based on the structure of the o-anisidine and a diacetate. However, in contrast to the ionophores of the group having the general Formula II they do not comprise aliphatically bound nitrogen. The two carboxyl ligand portions are bound to the aromatic nitrogen of the o-anisidine in the form of diethoxyacetate groups.

In the compounds of the invention having a group of the general Formula III it is preferred that n=2. $R_4$ preferably is alkyl having 1–2 C atoms. $R_5$ is advantageously located in a position para to the oxygen of the o-anisidine and is preferably H or ethoxy or Cl.

The ionophores of the compounds having a group of the general Formula IV exhibit similar advantages if compared to ionophores having a group of the general Formula III.

In the compounds of the invention having a group of the general Formula IV, $R_6$ preferably is methyl. $R_7$ advantageously is located in a position para to the oxygen of the o-anisidine and is preferably H.

Suitable luminophoric moieties L can be chemically bound to the ionophores of the invention via a —$(CH_2)_n$— spacer, wherein n preferably means the numbers 1 and 2 but can also be 0. Suitable luminophoric moieties are basically all luminophoric moieties which, in combination with the ionophores of the invention, afford a PET effect (see above).

Those skilled in the art will be aware that in order for a PET effect to materialize it is essential in particular that the electron donor of the ionophoric moiety be electronically decoupled from the electronic system of the luminophoric moiety. As is well known in the art, such electronic decoupling of the ionophoric and luminophoric moieties may be achieved in that the two moieties present are separated either by a spacer group, that is e.g. a $(CH_2)_n$ chain or—if n=0—by a virtual spacer (e.g. by pivoting the plane of the luminophoric moiety to the plane of the benzene ring). Hence, the function of the spacer is to oppose conjugation of the electron system of the ionophoric moiety with the electron system of the luminophoric moiety.

Electronic decoupling can be recognized e.g. from the fact that the wavelengths of the absorption and emission spectra of the luminophoric moiety do not change significantly with the calcium concentration.

Preferred luminophoric moieties are those that are capable of being excited by light of commercially available LEDs, that do not exhibit an inherent sensitivity towards pH (and $O_2$) and that in the form of the luminophore-ionophore compound exhibit stability in an aqueous environment over a prolonged time period. Further it is to be feasible for chemical groups to be added at the luminophoric or the ionophoric moiety, but preferably at the luminophore, by means of which chemical groups the luminophore-ionophore can be bound to a hydrophilic polymer matrix, preferably covalently.

Examples of suitable luminophoric moieties are luminescent derivatives of naphthalimide, of the difluorobora-3a,4a-s-indacenes and of xanthenones (e.g. fluoresceines and rhodamines).

In the compounds of the invention, the luminophoric moiety L is preferably located in a position para to the nitrogen.

The compounds of the invention of the general Formula I can be present as free dicarboxylic acids or in the form of the salts thereof. Advantageously, the compounds are present in the form of the dipotassium salt.

The invention also relates to an optical sensor for determining calcium ions in a sample, which sensor has a matrix comprising a compound having a luminophoric moiety and an ionophoric moiety, wherein the compound being used is a compound having a group of the general Formula I.

The invention further provides a method of determining calcium ions in a sample, wherein the calcium ions are brought into at least indirect contact with a compound having a luminophoric moiety and an ionophoric moiety, which ionophoric moiety reacts with the calcium ions present in the sample, wherein the luminophoric moiety changes its luminescence properties, whereupon the luminescence is measured and the calcium ions are determined using the test readings, wherein the compound being used is a compound having a group of the general Formula I.

In addition, the invention relates to the use of a compound having a group of the general Formula I in an optical sensor for the determination of calcium ions in a sample.

DETAILED DESCRIPTION OF THE DRAWINGS

DETAILED DESCRIPTION OF THE PREFERRED EMBODIMENTS

In the following, the invention will be described more fully by means of examples, wherein the synthesis and the properties of some compounds that are preferably used will be explained. Other compounds of the invention can be prepared in analogous manner by those skilled in the art.

1. Synthesis of ionophores of the invention

Figure 1:
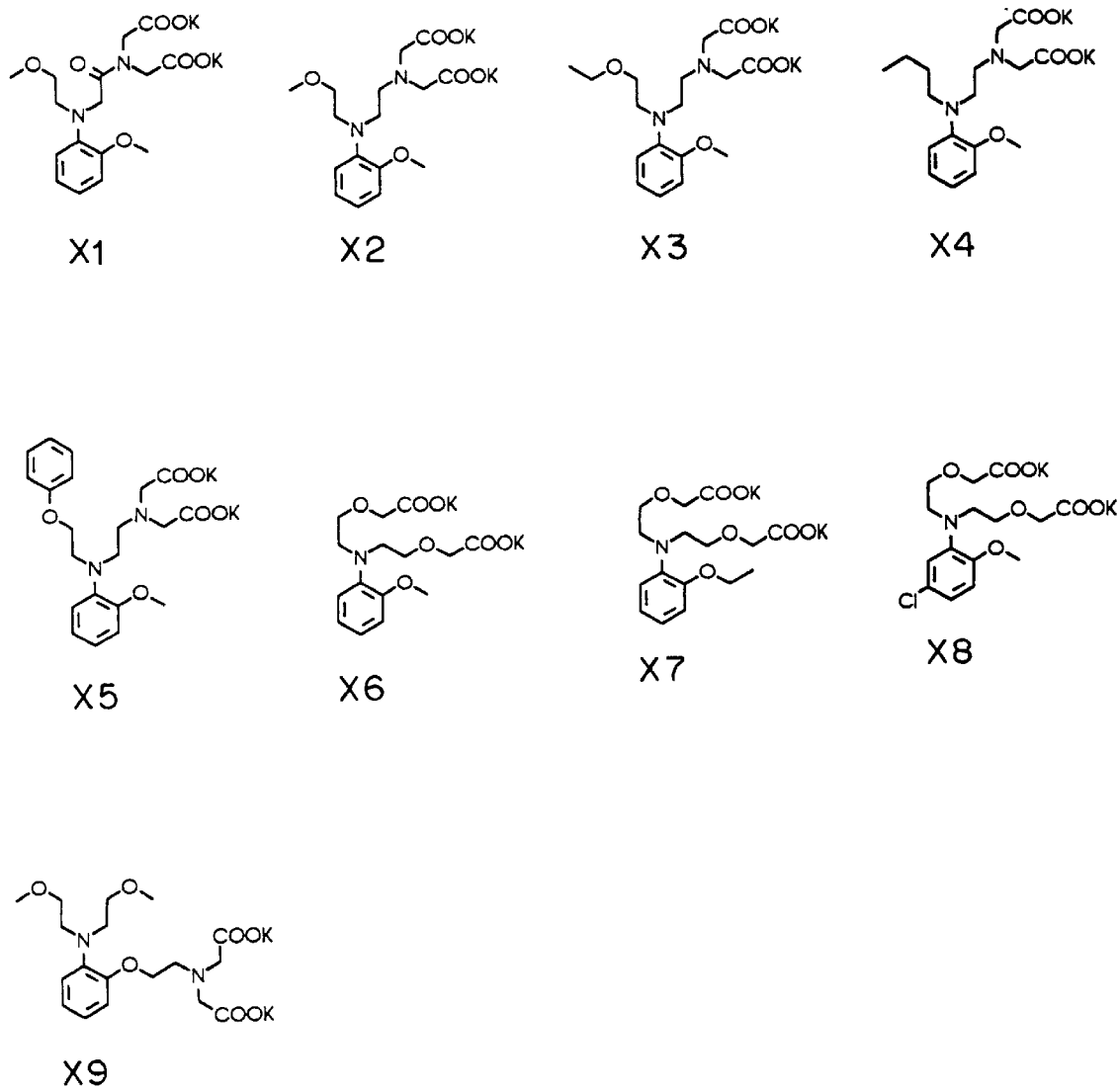
FIG. 1 is an illustration of calcium ionophores in accordance with invention.

FIG. 1 shows the formulae of the calcium ionophores (X1–X9) of the invention synthesized in the following examples.

Synthesis of the calcium ionophores of the invention can be divided into three general synthetic strategies.

Figure 2A:
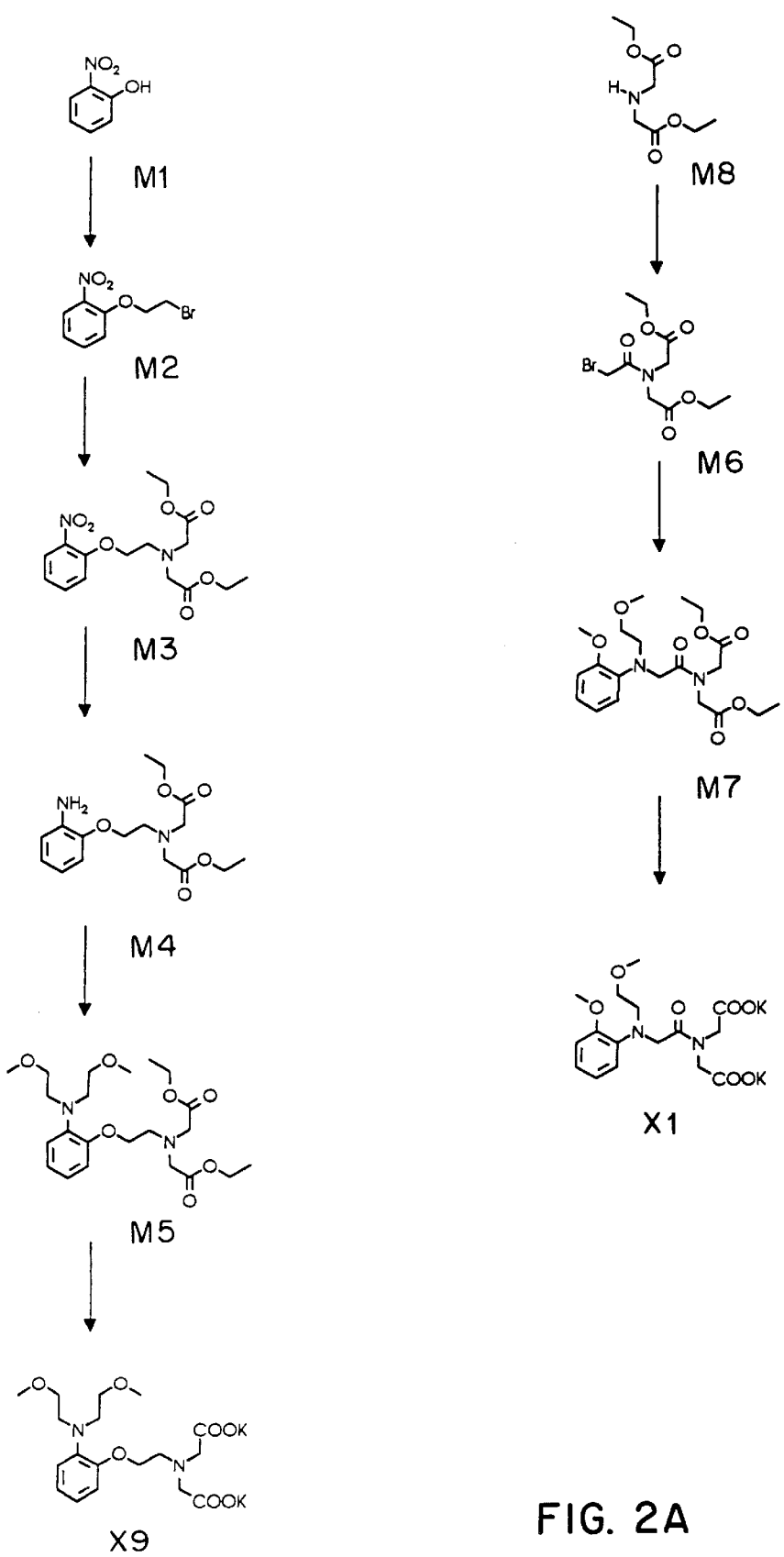
FIGS. 2A, 2B and 2C are illustrations of synthetic schemes for preparing calcium ionophores X1 and X9 shown in FIG. 1, X2, X3, X4 and X4 shown in FIG. 1, and X6, X7 and X8 shown in FIG. 1, respectively.
Figure 2B:
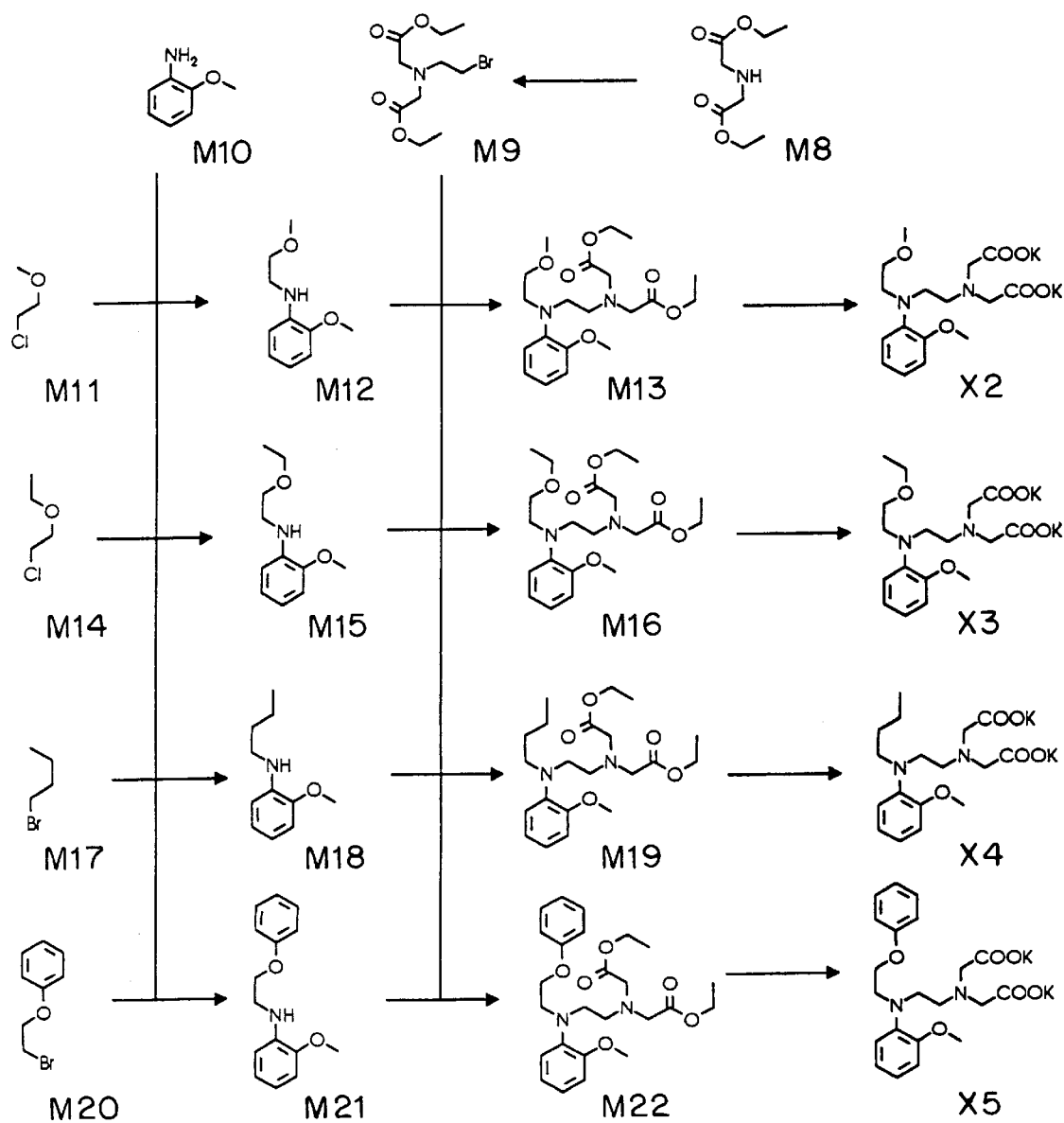

The first synthetic strategy is based on monoalkylation of o-anisidine which subsequently is alkylated with diethyl N-(2-bromoethyl)iminodiacetate (M9). Compounds X2, X3, X4 and X5 belong to this category. The synthetic scheme for these compounds is shown in FIG. 2B.

Figure 2C:
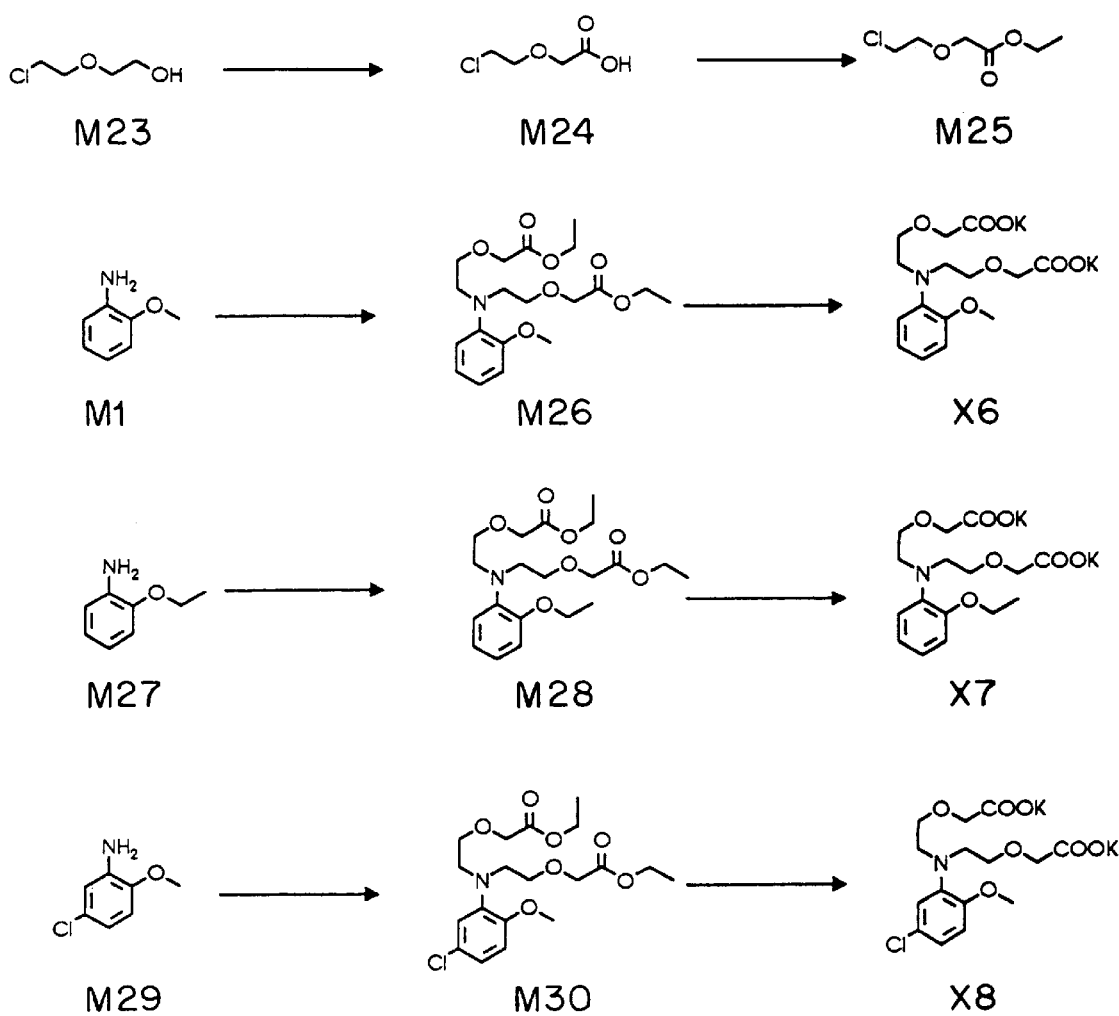

The second synthetic strategy is based on dialkylation of o-alkoxy anilines. The alkylation agent for compounds X6, X7 and X8 was ethyl 2-chloroethoxyacetate (M25). The synthetic scheme for these compounds is shown in FIG. 2C.

The third synthetic strategy including compounds X1 and X9 did not use the same intermediate. These compounds were prepared according to individual synthetic schemes shown in FIG. 2A.

1.1. Synthesis of potassium N-[2-(N',N'-dimethoxyethyl)aminophenoxyethyl]imino-N,N-diacetate (X9, see FIG. 2A)

1.1.1 2-(2-Bromoethoxy)-nitrobenzene (M2)

A suspension of 35.4 g (200 mmol) potassium 2-nitrophenolate, 112.7 g (600 mmol) 1,2-dibromoethane in 100 ml DMF was heated at 120° C. for 3 hours. The mixture was cooled and diluted with 400 ml $CHCl_3$, washed with 3×400 ml 2.5% $Na_2CO_3$ till the aqueous layer became almost colorless, was then washed with 400 ml saturated NaCl and dried over $Na_2SO_4$. The solvent was evaporated and the residue was triturated with 50 ml methanol, the resultant precipitate was filtered off (dimer). The filtrate was concentrated to afford 22.7 g oil, which solidified after cooling to room temperature. Upon recrystallizing from methanol/water (95/5, v/v), 17.8 g off-white crystals were obtained (yield: 36.2%).

$^1$H-NMR ($CDCl_3$), δ (ppm): 3.68 (t, 2H), 4.42 (t, 2H), 7.08 (m, 2H), 7.55 (m, 1H), 7.83 (m, 1H).

1.1.2 Diethyl-N-(2-nitrophenoxyethyl)imino-N,N-diacetate (M3)

A mixture of 2.46 g (10 mmol) M2, 2.08 g (11 mmol) diethyl iminodiacetate M8 (see FIG. 2B), 1.52 g (11 mmol) $K_2CO_3$, 0.83 g (5 mmol) KI and 10 ml DMF was heated at 85° C. for 20 hours, cooled and diluted with 50 ml $CHCl_3$ and 50 ml water. The organic phase was washed with 50 ml saturated NaCl and dried over $Na_2SO_4$. The solvent was evaporated to give 4.10 g crude oil. This oil was purified by a silica gel column with $CHCl_3$ and cyclohexane as eluant, wherein 2.68 g clear oil were obtained (yield: 76%).

$^1$H-NMR ($CDCl_3$), δ (ppm): 1.25 (t, 6H), 3.25 (t, 2H), 3.69 (s, 4H), 4.14 (m, 4H), 4.27 (t, 2H), 6.98–7.10 (m, 2H), 7.51 (m, 1H), 7.84 (m, 1H).

1.1.3. Diethyl N-(2-aminophenoxyethyl)imino-N,N-diacetate (M4)

2.60 g (7.3 mmol) of M3 and 0.26 g 10% Pd/C was suspended in 50 ml absolute ethanol, hydrogenated at 30 psi for 2 hours and filtered. The solvent was evaporated to afford 2.20 g light yellow oil (yield: 92%).

$^1$H-NMR ($CDCl_3$), δ (ppm): 1.25 (t, 6H), 3.20 (t, 2H), 3.65 (s, 6H, inc. $NH_2$), 4.18 (m, 6H), 4.27 (t, 2H), 6.70–6.80 (m, 4H, Ar.).

1.1.4. Diethyl-N-[2-(N',N'-dimethoxyethyl)aminophenoxyethyl]imino-N,N-diacetate (M5)

A suspension of 1.62 g (5 mmol) M4, 23.5 g (350 mmol) chloroethyl methyl ether, 1.65 g (12 mmol) $K_2CO_3$, 1.0 g (6 mmol) KI in 25 ml DMF was heated at 95° C. for 18 hours. Most of DMF and unreacted chloroethyl methyl ether were evaporated. The residue was dissolved in 100 ml $CHCl_3$ and 100 ml saturated NaCl. The organic phase was dried over $Na_2SO_4$. The solvent was evaporated to give 2.21 g oil. This crude oil was purified with silica gel 100 using $CHCl_3$ as eluant to afford 0.64 g pure product (yield: 29%).

$^1$H-NMR ($CDCl_3$), δ (ppm): 1.23 (t, 6H), 3.20 (t, 2H), 3.32 (t, 2H), 3.40 (t, 4H), 3.60 (t, 2H), 3.65 (s, 4H), 4.18 (m, 6H), 6.60–6.85 (m, 4H, Ar.).

1.1.5. Potassium N-[2-(N',N'-dimethoxyethyl)aminophenoxyethyl]imino-N,N-diacetate (X9)

0.25 ml water and 0.09 g (1.5 mmol) KOH were added to a solution of 0.22 g (0.5 mmol) M5 in 4.75 ml methanol. The resultant solution was heated to 60° C. for 5 min and then stirred at room temperature for 4 hours. Thin-layer chromatography showed that all ester was hydrolyzed. The concentration of X9 in this final solution was 100 mmol/l. 5 ml of this solution was diluted to 1000 ml with HEPES buffer (pH 7.3) containing 140 mmol/l $Na^+$, 5 mmol/l $K^+$ and 110 mmol/l $Cl^-$. The UV-absorption curves presented in FIG. 4 were measured with this solution spiked with different levels of $CaCl_2$.

1.2. Synthesis of potassium N-[2-(N'-methoxyethyl-N'-(2-methoxyphenyl)aminoacetyl)]-imino-N,N-diacetate (X1, see FIG. 2A)

1.2.1. Diethyl-N-(bromoacetyl)imino-N,N-diacetate (M6)

A solution of 9.44 g (60 mmol) bromoacetyl chloride in 25 ml $CH_2Cl_2$ was added to a solution of 9.5 g (50 mmol) diethyl iminodiacetate M8 (see FIG. 2B) and 6.07 g (60 mmol) triethylamine in 25 ml $CH_2Cl_2$ at 0° C. The resultant suspension was stirred at room temperature for 4 hours, diluted with 150 ml $CHCl_3$ and washed with 200 ml water, 3×200 ml 0.1 N HCl, 3×200 ml saturated $NaHCO_3$ and 200 ml saturated NaCl and dried over $Na_2SO_3$. The solvent was evaporated to give 12.6 g oil. This oil was purified with a silica gel column using CHCl₃/cyclohexane (1/1, v/v) as eluant to afford 9.25 g pure product (yield: 60%).

¹H-NMR (CDCl₃), δ (ppm): 1.25 (t, 6H), 2.10 (s, 2H), 4.20 (m, 8H).

1.2.2. Diethyl N-[2-(N'-methoxyethyl-N'-(2-methoxyphenyl)aminoacetyl)]-imino-N,N-diacetate (M7)

A suspension of 0.73 g (4 mmol) M12 (for synthesis see 1.3.2. and FIG. 2B), 1.86 g (6 mmol) M6 and 0.83 g (6 mmol) K₂CO₃ in 6 ml acetonitrile was heated at 85° C. for 18 hour The mixture was cooled and diluted with 30 ml CHCl₃ and 30 ml water. The organic layer was washed with 30 ml saturated NaCl and dried over Na₂SO₄. The solvent was evaporated to give 2.55 g crude product. This oil was purified with a column packed with 13 g silica gel and eluted with CHCl₃ to collect pure product, wherein 0.96 g were obtained (yield 59%).

¹H-NNIR (CDCl₃), δ (ppm): 1.25 (t, 6H), 3.40 (t, 2H), 3.50 (t, 2H), 3.80 (s, 3H), 4.05 (s, 3H), 4.08 (s, 4H), 4.12 (q, 4H), 4.50 (s, 2H), 6.80–7.10 (m, 4H, Ar.).

1.2.3. Potassium N-[2-(N'-methoxyethyl-N'-(2-methoxyphenyl)aminoacetyl)]-imino-N,N-diacetate (X1)

As procedure similar to that described in Section 1.1.5. above was used to hydrolyze M7 and to obtain a solution of X1, which was used for absorption measurements.

1.3. Synthesis of potassium N-[2-(N'-methoxyethyl-N'-(2-methoxyphenyl)aminoethyl)]-imino-N,N-diacetate (X2, see FIG. 2B)

1.3.1. Diethyl N-(2-bromoethyl)imino-N,N-diacetate (M9)

A solution of 9.5 g (50 mmol) diethyl iminodiacetate M8, 94.0 g (500 mmol) 1,2-dibromoethane and 7.8 g (60 mmol) diisopropylethylamine was heated at 85° C. for 18 hours. Subsequently it was cooled and diluted with 100 ml CHCl₃ and 100 ml water. The organic phase was washed with 2×200 ml water and 200 ml saturated NaCl and dried over Na₂SO₄. Solvent and unreacted dibromoethane were evaporated, the residue was purified with a silica gel column using CHCl₃/cyclohexane (1/1, v/v) as eluant. 4.0 g clear oil was obtained (yield: 27%).

¹H-NMR (CDCl₃), δ (ppm): 1.23 (t, 6H), 3.15 (t, 2H), 3.40 (t, 2H), 3.60 (s, 4H), 4.08 (m, 4H).

1.3.2. N-methoxyethyl-2-anisidine (M12)

A suspension of 24.6 g (200 mmol) o-anisidine M10, 20.8 g (220 mmol) chloroethyl methyl ether M11, 30.4 g (220 mmol) K₂CO₃ and 18.3 g (110 mmol) KI in 110 ml DMF was heated at 95° C. for 24 hours. DMF was evaporated, and the residue was digested with 100 ml CHCl₃, filtered, and the precipitate washed with 2×50 ml CHCl₃. The solvent was evaporated to give 41.2 g crude oil. This oil was purified by a plug packed with 184 g silica gel 100 with CHCl₃/cyclohexane (1:1, v/v) as eluant, to afford 23.5 g pure product (yield: 65%).

¹H-NMR (CDCl₃), δ (ppm): 3.28 (t, 2H), 3.40 (s, 3H), 3.65 (t, 2H), 3.78 (s, 3H), 6.35 (d, 1H), 6.60 (t, 1H), 6.78 (m, 2H).

1.3.3. Diethyl N-[2-(N'-methoxyethyl-N'-(2-methoxyphenyl)aninoethyl)]-imino-N,N-diacetate (M13)

A suspension of 0.36 g (2 mmol) M12, 0.65 g (2.2 mmol) M9 and 0.30 g (2.2 mmol) K₂CO₃ in 2 ml DMF was heated at 85° C. for 18 hours. The mixture was cooled and diluted with 20 ml CHCl₃ and 20 ml water. The organic layer was washed with 20 ml saturated NaCl and dried over Na₂SO₄. The solvent was evaporated to give 1.05 g crude product. This oil was purified with a column packed with 5 g silica gel, wherein elution was carried out with CHCl₃ to remove unreacted M12 and with CHCl₃/ethyl acetate (4/1, v/v) to collect the pure product. 0.33 g pure product were obtained (yield: 51%). ¹H-NMR (CDCl₃), δ (ppm): 1.25 (t, 6H), 2.85 (t, 2H), 3.30 (s, 3H), 3.35 (m, 4H), 3.40 (t, 2H), 3.60 (s, 4H), 3.80 (s, 3H), 4.18 (q, 4H), 6.80–7.05 (m, 4H, Ar.).

1.3.4. Potassium N-[2-(N'-methoxyethyl-N'-(2-methoxyphenyl)aminoethyl)]-imino-N,N-diacetate (X2)

A procedure similar to that described in Section 1.1.5. above was used to hydrolyze M13 and to obtain a solution of X2, which was used for absorption measurements.

1.4. Synthesis of potassium N-[2-(N'-ethoxyethyl-N'-(2-methoxyphenyl)aminoethyl)]-imino-N,N-diacetate (X3, see FIG. 2B)

1.4.1. N-ethoxyethyl-2-anisidine (M15)

A suspension of 12.3 g (100 mmol) o-anisidine M10, 11.9 g (110 mmol) chloroethyl ethyl ether M14, 15.2 g (110 mmol) K₂CO₃ and 9.1 g (55 mmol) KI in 55 ml DMF was heated at 95° C. for 18 hours. DMF was evaporated and the residue was dissolved in 100 ml CHCl₃ and 100 ml saturated NaCl. The organic layer was dried over Na₂SO₄. The solvent was evaporated to give 19.4 g crude oil. The crude oil was purified with a plug packed with 84 g silica gel 100 with CHCl₃/cyclohexane (1:1, v/v) as eluant to afford 7.85 g pure product (yield: 40%).

¹H-NMR (CDCl₃), δ (ppm): 1.25 (t, 3H), 3.30 (t, 2H), 3.58 (q, 2H), 3.65 (t, 2H), 3.78 (s, 3H), 6.35 (d, 1H), 6.60 (t, 1H), 6.78 (m, 2H).

1.4.2. Diethyl-N-[2-(N'-ethoxyethyl-N'-(2-methoxyphenyl) aminoethyl)]-imino-N,N-diacetate (M16)

A suspension of 0.59 g (3 mmol) M15, 1.33 g (4.5 mmol) M9 (for synthesis see 1.3.1.) and 0.62 g (4.5 mmol) K₂CO₃ in 3 ml DMF was heated at 85° C. for 18 hours. The mixture was cooled and diluted with 50 ml CHCl₃ and 20 ml water. The organic layer was washed with 50 ml saturated NaCl and dried over Na₂SO₄. The solvent was evaporated to give 1.25 g crude product. This oil was purified with a column packed with 6 g silica gel, wherein elution was carried out with CHCl₃ to remove unreacted M15 and with CHCl₃/ethyl acetate (4/1, v/v) to collect the pure product. 0.25 g pure product were obtained (yield: 26%).

¹H-NMR (CDCl₃), δ (ppm): 1.25 (m, 8H), 2.85 (t, 2H), 3.30 (q, 2H), 3.35 (m, 4H), 3.40 (t, 2H), 3.60 (s, 4H), 3.80 (s, 3H), 4.18 (q, 4H), 6.80–7.05 (m, 4H, Ar.).

1.4.3. Potassium N-[2-(N'-ethoxyethyl-N'-(2-methoxyphenyl)aminoethyl)]-imino-N,N-diacetate (X3)

A procedure similar to that described in Section 1.1.5. above was used to hydrolyze M16 and obtain a solution of X3, which was used for absorption measurements.

1.5. Synthesis of potassium N-[2-(N'-butyl-N'-(2-methoxyphenyl)aminoethyl)]-imino-N,N-diacetate (X4, see FIG. 2B)

1.5.1. N-butyl-2-anisidine (M18)

A suspension of 6.2 g (50 mmol) o-anisidine M10, 7.5 g (55 mmiol) 1-bromobutane M17, 7.6 g (55 mmol) K₂CO₃ and 0.91 g (5.5 mmol) KI in 25 ml DMF was heated at 95° C. for 24 hours. DMF was evaporated and the residue was dissolved in 100 ml CHCl₃ and 100 ml saturated NaCl. The organic layer was dried over Na₂SO₄. The solvent was evaporated to give 9.4 g crude oil. This oil was purified by a plug packed with 45 g silica gel 100 using cyclohexane as eluant, wherein 4.8 g pure product were obtained (yield: 55%).

¹H-NMR (CDCl₃), δ (ppm): 0.95 (t, 3H), 1.42 (m, 2H), 1.62 (m, 2H), 3.05 (m, 2H), 3.85 (s, 3H), 6.60–7.00 (m, 4H).

1.5.2. Diethyl-N-[2-(N'-butyl-N'-(2-methoxyphenyl) aminoethyl)]-imino-N,N-diacetate (M19)

A suspension of 0.36 g (2 mmol) M18, 0.65 g (2.2 mmol) M9 (for synthesis see 1.3.1.) and 0.30 g (2.2 mmol) K₂CO₃ in 2 ml DMF was heated at 85° C. for 18 hours. The mixture was cooled and diluted with 25 ml CHCl₃ and 25 ml water.

The organic layer was washed with 25 ml saturated NaCl and dried over $Na_2SO_4$. The solvent was evaporated to give 1.05 g crude product. This crude product was purified with a column packed with 5.5 g silica gel, wherein elution was carried out with $CHCl_3$ to remove unreacted M18 and with $CHCl_3$/ethyl acetate (4/1, v/v) to collect the pure product. 0.31 g pure product were obtained (yield: 39%).

$^1$H-NMR ($CDCl_3$), δ (ppm): 0.92 (t, 3H), 1.20 (t, 6H), 1.25 (m, 2H), 1.40 (m, 2H), 2.80 (t, 2H), 3.05 (t, 2H), 3.20 (t, 2H), 3.55 (s, 4H), 3.80 (s, 3H), 4.18 (q, 4H), 6.80–7.05 (m, 4H, Ar.).

1.5.3. Potassium N-[2-(N'-butyl-N'-(2-methoxyphenyl)aminoethyl)]-imino-N,N-diacetate (X4)

A procedure similar to that described in Section 1.1.5. above was used to hydrolyze M19 and obtain a solution of X4, which was used for absorption measurements.

1.6. Synthesis of potassium N-[2-(N'-phenoxyethyl-N'-(2-methoxyphenyl)aminoethyl)]-imino-N,N-diacetate (X5, see FIG. 2B)

1.6.1. N-(2-phenoxyethyl)-2-anisidine (M21)

A suspension of 6.2 g (50 mmol) o-anisidine M10, 12.1 g (60 mmol) β-bromophenetole M20 and 8.3 g (60 mmol) $K_2CO_3$ in 25 ml acetonitrile was heated at reflux for 18 hours. The mixture was cooled, diluted with 100 ml $CHCl_3$ and washed with 100 ml water and 100 ml saturated NaCl. The organic layer was dried over $Na_2SO_4$. The solvent was evaporated to give 14.5 g crude oil. This oil was purified by a plug packed with 60 g silica gel 100 with cyclohexane as eluant, wherein 6.4 g pure product were obtained (yield: 51%).

$^1$H-NMR ($CDCl_3$), δ (ppm): 3.45 (t, 2H), 3.85 (s, 3H), 4.05 (t, 2H), 6.80–7.20 (m, 9H).

1.6.2. Diethyl N-[2-(N'-phenoxyethyl-N'-(2-methoxyphenyl)aminoethyl)]-imino-N,N-diacetate (M22)

A suspension of 0.97 g (4 mmol) M21, 1.78 g (6 mmol) M9 (for synthesis see 1.3.1.) and 0.83 g (6 mmol) $K_2CO_3$ in 4 ml acetonitrile was heated at 85° C. for 18 hours. The mixture was cooled and diluted with 50 ml $CHCl_3$ and 50 ml water. The organic layer was washed with 50 ml saturated NaCl and dried over $Na_2SO_4$. The solvent was evaporated to give 2.60 g crude product. This oil was purified with a column packed with 13 g silica gel, wherein elution was carried out with $CHCl_3$/cyclohexane (1/1, v/v) to remove unreacted M21 and with $CHCl_3$/ethyl acetate (4/1, v/v) to collect the pure product. 1.20 g pure product were obtained (yield: 66%).

$^1$H-NMR ($CDCl_3$), δ (ppm): 1.25 (t, 6H), 2.85 (t, 2H), 3.20 (t, 2H), 3.45 (t, 2H), 3.60 (s, 4H), 3.80 (s, 3H), 4.00 (t, 2H), 4.18 (q, 4H), 6.80–7.05 (m, 4H, Ar.).

1.6.3. Potassium N-[2-(N'-phenoxyethyl-N'-(2-methoxyphenyl)aminoethyl)]-imino-N,N-diacetate (X5)

A procedure similar to that described in Section 1.1.5. above was used to hydrolyze M22 and obtain a solution of X5, which was used for absorption measurements.

1.7. Synthesis of potassium-o-anisidine-N,N-diethoxyacetate (X6, see FIG. 2C)

1.7.1. 2-Chloroethoxyacetic acid (M24)

100 g (800 mmol) 2-chloroethoxyethanol M23 was added slowly into 500 ml conc. $HNO_3$ (70%) at 55° C. within 8 hours. The solution was stirred at room temperature for 18 hours and heated in a boiling water bath for 1 hour, cooled and poured into 500 ml icy water. The diluted solution was extracted 8× with 11 $CHCl_3$. All extracts were combined and evaporated to afford 54.2 g oil (yield: 49%). This oil was used directly for the next esterification without fuirther purification.

1.7.2. Ethyl-2-chloroethoxyacetate (M25)

54.1 g (390 mmol) M24 obtained from the preceding reaction step was dissolved in 380 ml absolute ethanol and 9 ml conc. $H_2SO_4$ was added. The mixture was heated at reflux for 18 hours. Most of the ethanol was evaporated and the residue was dissolved in 400 ml $CHCl_3$/100 ml water and basified with powder $NaHCO_3$. The organic phase was washed with 2×400 ml saturated $NaHCO_3$ and dried over $Na_2SO_4$. The solvent was evaporated to afford 58.3 g clear oil (yield: 89%).

$^1$H-NMR ($CDCl_3$), δ (ppm): 1.25 (t, 3H), 3.68 (t, 2H), 3.82 (t, 2H), 4.15 (s, 2H), 4.20 (q, 4H).

1.7.3. Diethyl-o-anisidine-N,N-diethoxyacetate (M26)

A suspension of 0.37 g (3 mmol) o-anisidine M10, 1.34 g (8 mmol) ethyl-2-chloroethoxyacetate M25, 1.10 g (8 mmol) $K_2CO_3$ and 0.67 g (4 mmol) KI in 3 ml DMF was heated at 95° C. for 7 hours. Thin-layer chromatography showed that there was a lot of mono-alkylated product. 1.34 g (8 mmol) more ethyl-2-chlorethoxyacetate M25 and 1.10 g (8 mmol) more $K_2CO_3$ were added. Heating was continued for another 18 hours. The mixture was cooled and diluted with 50 ml water/50 ml $CHCl_3$. The organic phase was washed with 50 ml saturated NaCl and dried over $Na_2SO_4$. The solvent was evaporated to give 1.08 g crude oil. This oil was purified with a plug packed with 5 g silica gel 100 using cyclohexane/$CHCl_3$ as eluant to remove front impurities and then $CHCl_3$/ethylacetate (4/1, v/v) were used, wherein 0.38 g light yellow oil were obtained (yield: 32%).

$^1$H-NMR ($CDCl_3$), δ (ppm): 1.22 (t, 6H), 3.42 (t, 3H), 3.60 (t, 3H), 3.80 (s, 3H), 4.02 (s, 4H), 4.15 (q, 4H), 6.80–7.05 (m, 4H).

1.7.4. Potassium-o-anisidine-N,N-diethoxyacetate (X6)

A procedure similar to that described in Section 1.1.5. above was used to hydrolyze M26 and obtain a solution of X6, which was used for absorption measurements.

1.8. Synthesis of potassium o-phenetidine-N,N-diethoxyacetate (X7, see FIG. 2C)

1.8.1. Diethyl o-phenetidine-N,N-diethoxyacetate (M28)

A suspension of 0.68 g (5 mmol) o-phenitidine M27, 2.50 g (15 mmol) ethyl 2-chloroethoxyacetate M25 (for synthesis see 1.7.), 2.07 g (15 mmol) $K_2CO_3$ and 1.25 g (7.5 mmol) KI in 3 ml DMF was heated at 95° C. for 20 hours. The mixture was cooled and diluted with 80 ml water/80 ml $CHCl_3$. The organic phase was washed with 80 ml saturated NaCl and dried over $Na_2SO_4$. The solvent was evaporated to give 2.05 g crude oil. This oil was purified with a plug packed with 5 g silica gel 100 using cyclohexane/$CHCl_3$ as eluant to remove front impurities and then using $CHCl_3$/ethyl acetate (4/1, v/v). 0.84 g light yellow oil were obtained (yield: 42%).

$^1$H-NMR ($CDCl_3$), δ (ppm): 1.22 (t, 6H), 1.42 (t, 3H), 3.42 (t, 3H), 3.62 (t, 3H), 4.02 (q, 2H), 4.05 (s, 4H), 4.20 (q, 4H), 6.80–7.05 (m, 4H).

1.8.2. Potassium o-phenetidine-N,N-diethoxyacetate (X7)

A procedure similar to that described in Section 1.1.5. above was used to hydrolyze M28 and obtain a solution of X7, which was used for absorption measurements.

1.9. Synthesis of potassium 5-chloro-o-anisidine-N,N-diethoxyacetate (X8, see FIG. 2C)

1.9.1. Diethyl-5-chloro-o-anisidine-N,N-diethoxyacetate (M30)

A suspension of 0.78 g (5 mmol) 5-chloro-2-methoxyaniline M29, 2.50 g (15 mmol) ethyl-2-chloroethoxyacetate M25 (for synthesis see 1.7.), 2.07 g (15 mmol) $K_2CO_3$ and 1.25 g (7.5 mmol) KI in 30 ml DMF was heated at 95° C. for 18 hours. DMF was evaporated and the residue was diluted with 80 ml water/80 ml $CHCl_3$. The organic phase was washed with 80 ml saturated NaCl and dried over $Na_2SO_4$. The solvent was evaporated to give 2.70 g crude oil. This oil was purified with a plug packed with 5 g silica gel 100 using cyclohexane/$CHCl_3$ as eluant to remove front impurities and then using $CHCl_3$/ethylacetate (4/1, v/v). 0.54 g light yellow oil were obtained (yield: 26%).

$^1$H-NMR ($CDCl_3$), δ (ppm): 1.25 (t, 6H), 3.45 (t, 3H), 3.62 (t, 3H), 3.80 (s, 3H), 4.02 (s, 4H), 4.20 (q, 4H), 6.60–7.05 (m, 3H).

1.9.2. Potassium 5-chloro-o-anisidine-N,N-diethoxyacetate (X8)

A procedure similar to that described in Section 1.1.5. above was used to hydrolyze M30 and obtain a solution of X8, which was used for absorption measurements.

2. Synthesis of luminophore-ionophores of this invention

Luminophore-ionophores based on naphthalimide were prepared by two different methods. The synthetic schemes are represented in FIGS. 3A and 3B.

Figure 3A:
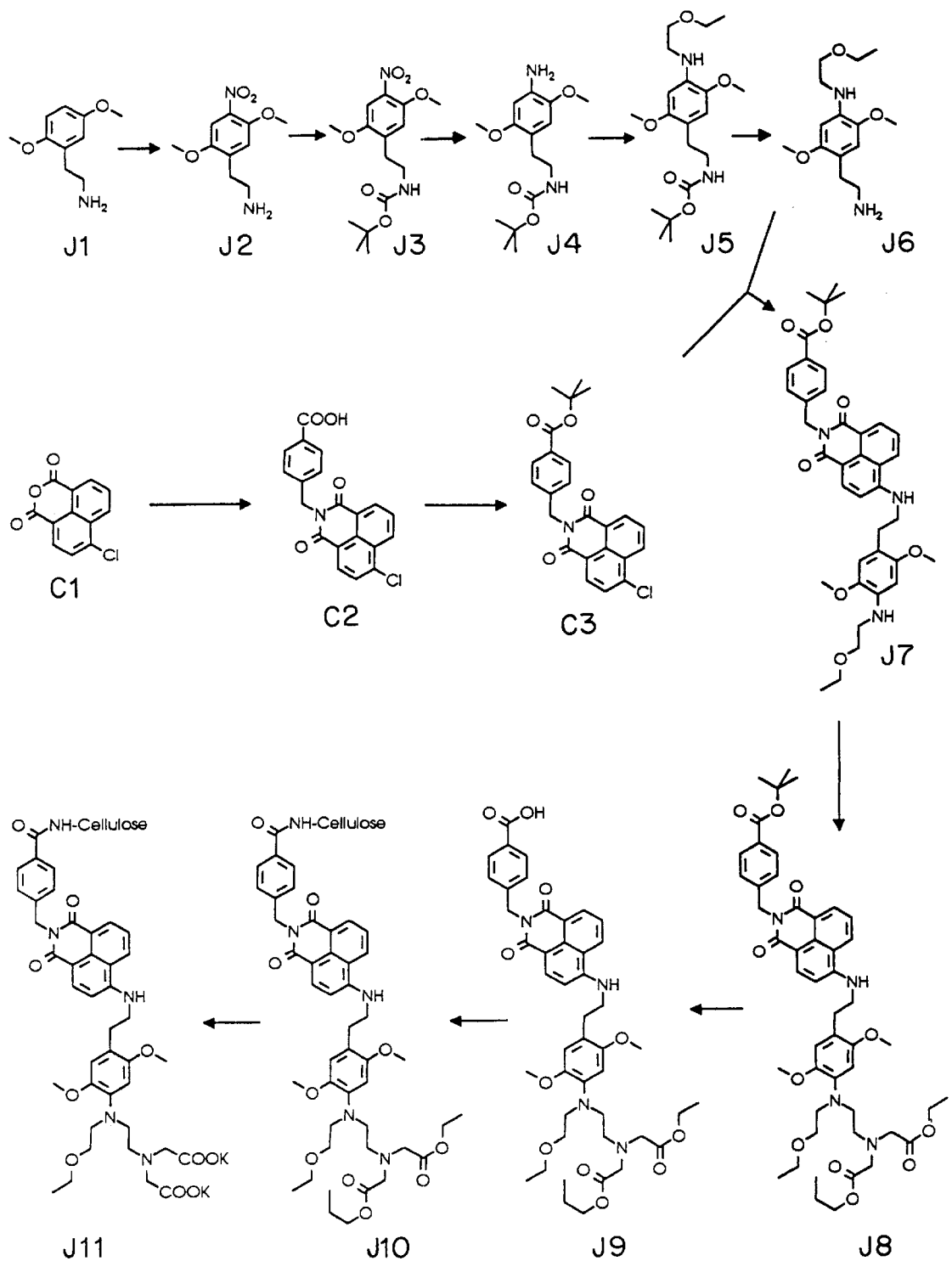
FIGS. 3A and 3B are illustration of synthetic schemes for preparing a luminophore-ionophore according to the invention starting from 2, 5-dimetlioxyphenethylamine and 2, 5-dihydroxybenzaldehyde, respectively.
Figure 3B:
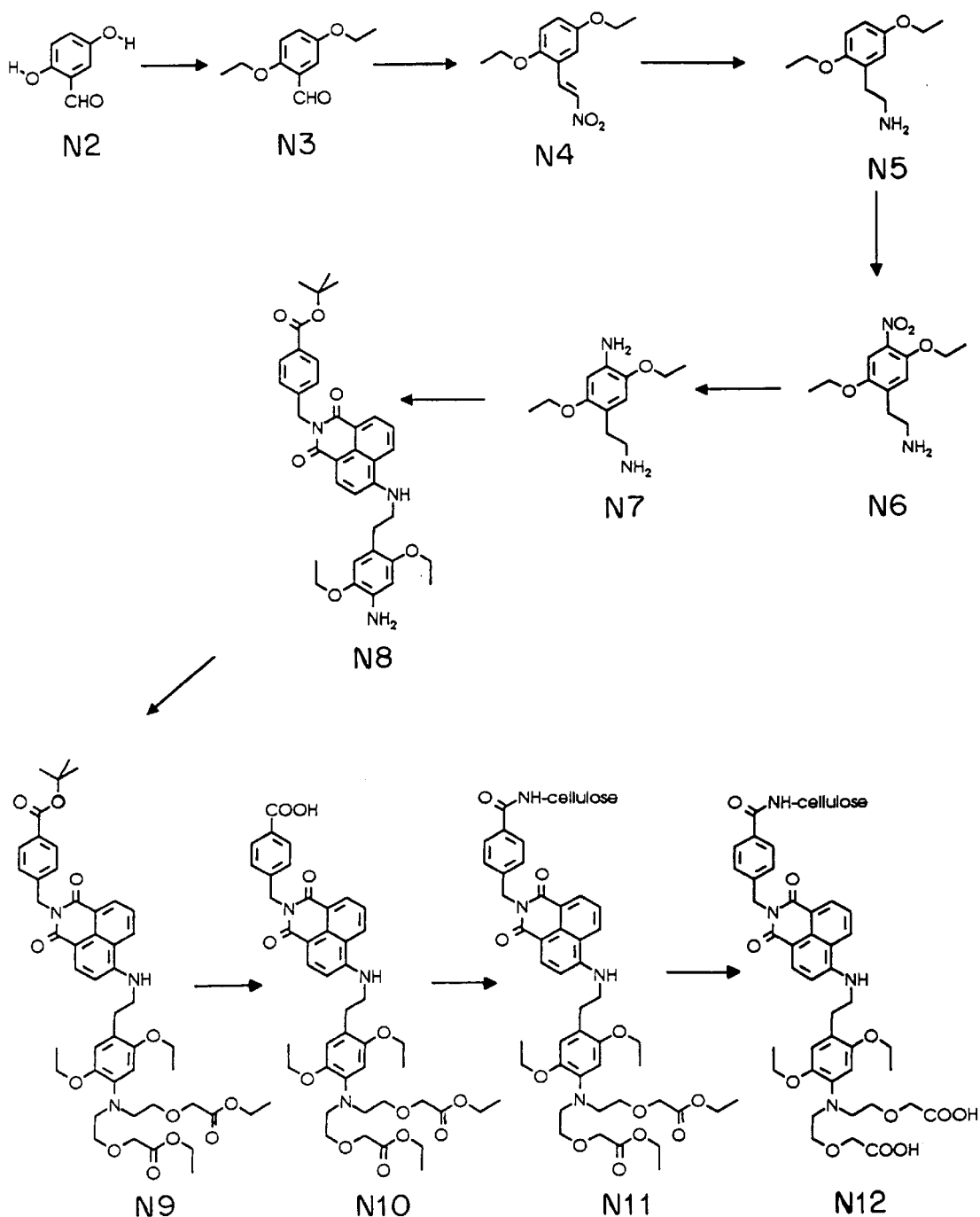

A luminophore-ionophore using X3* as ionophore (corresponding to X3 in FIG. 1, except that in a position para to the oxygen of the o-anisidine H is replaced by methoxy) was synthesized starting from a commercially available precursor, 2,5-dimethoxyphenethylamine J1 (FIG. 3A). This compound was nitrated in a $HNO_3$/HCl mixture, followed by BOC-protection (BOC=t-butoxycarbonyl), hydrogenation, monoalkylation and deprotection, and was then coupled to the 4-chloronaphthalimide derivative C3, which contains a t-butyl protected carboxylic acid group. The resultant luminophore J7 was alkylated with M9 (see FIG. 2B) to give the triester J8. The t-butylester was removed by trifluoroacetic acid (TFA) and the free carboxy group was used for immobilization of J9 on aminocellulose. The ethyl ester was hydrolyzed in aqueous KOH to obtain the final product J11.

According to the same synthetic scheme there was also prepared a luminophore-ionophore using X2* (corresponding to X2 in FIG. 1, except that in a position para to the oxygen of the o-anisidine H is replaced by methoxy) as ionophore.

Another luminophore-ionophore using X7* as ionophore (corresponding to X7 in FIG. 1, except that in a position para to the oxygen of the o-anisidine H is replaced by ethoxy), was prepared from 2,5-dihydroxybenzaldehyde N2 as starting material (FIG. 3B) because the ethyl analog of J1 was not commercially available. N2 was alkylated with iodoethane and condensed with nitromethane to obtain the nitrostyrene derivative N4, which was reduced to the phenethylamine derivative N5. N5 was nitrated, hydrogenated and coupled to the 4-chloronaphthalimide derivative C3. The resultant amine N8 was alkylated with M25 (for synthesis see 1.7. and FIG. 2C) to obtain the triester N9, which was deprotected, immobilized on aminocellulose and hydrolyzed to obtain the final product N12.

2.1. Synthesis of a luminophore-ionophore using X3* as ionophore 2.1.1. 4-Nitro-2,5-dimethoxyphenethylamine (J2)

45.5 g (250 mmol) 2,5-dimethoxyphenethylamine J1 was mixed with 40 ml water and cooled to 0° C. while 30 ml conc. HCl was added slowly. The resultant milky emulsion was cooled to 0 to 5° C., and 65 ml conc. $HNO_3$ was added slowly and carefully within about 2 hours, keeping the temperature below 10° C. The mixture solidified when about half of the $HNO_3$ had been added. 50 ml icy water was added to render the mixture stirrable. Then the rest of the $HNO_3$ was added. The mixture was warmed up to room temperature and stirred at room temperature for 3 hours, was basified with 40% NaOH to pH>12 and then extracted with 2×11 $CHCl_3$. The $CHCl_3$ extraction was back washed with 3×110.5 M NaOH and dried over 15 g $K_2CO_3$. The solvent was evaporated to afford 49.8 g orange oil (yield: 88%), which crystallized when cooled.

$^1$H-NMR ($CDCl_3$), δ (ppm): 1.30 (br.s, 2H), 2.80 (t, 2H), 2.95 (t, 2H), 3.80 (s, 3H), 3.92 (s, 3H), 6.90 (s, 1H), 7.20 (s, 1H).

2.1.2. N-t-butoxycarbonyl-4-nitro-2,5-dimethoxyphenethylamine (J3)

To a solution of 22.6 g (100 mmol) 4-nitro-2,5-dimethoxyphenethylamine J2 and 15.5 g (120 mmol) triethylamine in 125 ml $CHCl_3$ was added 26.2 g (120 mmol) di-t-butyl dicarbonate in 25 ml $CHCl_3$. The mixture was stirred at room temperature for 15 min, washed with 3×200 ml 0.4 M HCl and dried over $Na_2SO_4$. The solvent was evaporated to give 36 g oil. This oil was dissolved in 20 ml ethyl acetate, then 200 ml hexane was added, the resultant precipitate was filtered, washed with 2×100 ml hexane and dried at room temperature for 18 hours to afford 27.4 g light yellow fibrous powder (yield: 84%).

$^1$H-NMR ($CDCl_3$), δ (ppm): 1.40 (s, 9H), 2.82 (t, 2H), 3.35 (t, 2H), 3.80 (s, 3H), 3.90 (s, 3H1), 6.90 (s, 1H), 7.20 (s, 1H).

2.1.3. N-t-butoxycarbonyl-4-amino-2,5-dimethoxyphenethylamine (J4)

27 g (83 mmol) N-t-butoxycarbonyl-4-nitro-2,5-dimethoxyphenethylamine J3 was dissolved in 300 ml methanol, and 1.5 g 10% palladium on carbon black was added. This suspension was hydrogenated at 2.2 atm. for 18 hours till no further hydrogen uptake was observed. The catalyst was filtered off and the solvent was evaporated to afford 22.3 g white powder (yield: 98%). $^1$H-NMR ($CDCl_3$), δ (ppm): 1.40 (s, 9H), 1.55 (s, 2H), 2.65 (t, 2H), 3.25 (t, 2H), 3.70 (s, 3H), 3.80 (s, 31H), 6.30 (s, 1H), 6.58 (s, 1H).

2.1.4. N-t-butoxycarbonyl-4-(N'-ethoxyethyl)amino-2,5-dimethoxyphenethylamine (J5)

A mixture of 11.9 g (40 mmol) J4, 5.2 g (48 mmol) chloroethyl ethyl ether M14 (see FIG. 2B), 11.6 g (48 mmol) $K_2CO_3$, 4.0 g (24 mmol) KI and 20 ml DMF was heated at 95° C. for 18 hours. DMF was evaporated and the residue was dissolved in 200 ml $CHCl_3$ and 200 ml water. The organic layer was washed with 200 ml saturated NaCl and dried over $Na_2SO_4$. The solvent was evaporated to give 12 g oil. This oil was purified by a plug packed with 60 g silica gel 100 using cyclohexane as eluant, wherein 2.65 g pure product was obtained (yield: 18%).

$^1$H-NMR ($CDCl_3$), δ (ppm): 1.25 (t, 3H), 1.40 (s, 9H), 1.55 (s, 2H), 2.65 (t, 2H), 3.30 (m, 4H), 3.55 (q, 2H), 3.65 (t, 2H), 3.70 (s, 3H), 3.80 (s, 3H), 4.45 (br.s, 1H), 4.70 (br.s, 1H), 6.25 (s, 1H), 6.55 (s, 1H).

2.1.5. 4-(N-ethoxyethyl)amino-2,5-dimethoxyphenethylamine (J6)

2.60 g (7.1 mmol) J5 was dissolved in a mixture of 10 ml trifluoroacetic acid and 1 ml water. The mixture was stirred at room temperature for 15 min, diluted with 20 ml water, basified with saturated $K_2CO_3$ to pH~12 and extracted with 2×40 ml $CHCl_3$. The extraction was dried over $K_2CO_3$. The solvent was evaporated to afford 1.78 g oil (yield: 92%).

$^1$H-NMR ($CDCl_3$), δ (ppm): 1.25 (t, 3H), 1.60 (br. 2H), 2.65 (t, 2H), 2.90 (t, 3H), 3.30 (t, 2H), 2.90 (t, 3H), 3.30 (t, 2H), 3.55 (q, 2H), 3.70 (t, 2H), 3.80 (s, 3H), 3.85 (s, 3H), 4.45 (br.s, 1H), 6.30 (s, 1H), 6.60 (s, 1H).

2.1.6. 4-Chloro-1,8-naphthalimidylrnethylbenzoic acid (C2)

46.4 g (200 mmol) 4-chloro-1,8-naphthalic anhydride C1 and 30.2 g (200 mmol) 4-aminomethyl benzoic acid were suspended in 1 l DMF, stirred at room temperature for 16 hours and then at 60° C. for 6 hours. The mixture was poured into 3 l water and the pH adjusted to 4 with 6 N HCl. The resultant precipitate was filtered and dried at 60° C. for 18 hours to afford 36 g off-white powder (yield: 51%).

$^1$H-NMR (CDCl$_3$), δ (ppm): 5.30 (s, 2H), 7.45 (d, 2H), 7.85 (d, 2H), 8.02 (q, 2H), 8.45(d, 1H), 8.60 (t, 2H).

2.1.7. t-Butyl-4-chloro-1,8-naphthalimidylmethylbenzoate (C3)

To a suspension of 29.2 g (80 mmol) C2 in 320 ml DMF, stirred at 40° C. under a stream of nitrogen, 52.0 g (320 mmol) 1,1'-carbonyldiimidazole was added slowly during 20 min. The suspension turned into a clear solution and became turbid again in 15 min. Then the mixture was heated to 70° C. and after addition of 52 ml (1600 mmol) t-butanol and 48 ml (320 mmol) 1,8-diazabicyclo[5,4,0]undec-7-ene (DBU) was kept at this temperature for 18 hours. The mixture was cooled and poured into 2.0 l icy 1 N HCl under vigorous stirring. The resultant precipitate was filtered, washed with 2×300 ml 1 N HCl, and after drying in a desiccator with P$_2$O$_5$ for 18 hours it afforded 28.5 g crude product. This crude product was purified with a silica gel column using CHCl$_3$/cyclohexane as eluant to give 12.0 g white powder (yield: 36%).

$^1$H-NMR (CDCl$_3$), δ (ppm): 1.50 (s, 9H), 5.30 (s, 2H), 7.45 (d, 2H), 7.80 (d, 2H), 8.05 (q, 2H), 8.50 (d, 1H), 8.60 (t, 2H).

2.1.8. t-Butyl 4-{4-[4-(N-ethoxyethylamino)-2,5-dimethoxyphenylethyl amino]-1,8-naphthalimidylmethyl} benzoate (J7)

A suspension of 1.70 g (6.3 mmol) J6 and 0.88 g (2.1 mmol) C3 in 2.2 ml N-methylpyrrolidinone (NMP) was heated at 85° C. for 18 hours. The mixture was cooled and poured into 45 ml water. The resultant precipitate was filtered and washed with 3×20 ml water and dried over P$_2$O$_5$ for 18 hours to obtain 1.2 g crude product. The crude product was purified with a silica gel column using CHCl$_3$ as eluant to afford 0.92 g pure product (yield: 67%).

$^1$H-NMR (CDCl$_3$), δ (ppm): 1.20 (t, 3H), 1.55 (s, 9H), 3.05 (t, 2H), 3.35 (t, 2H), 3.55 (m, 4H), 3.70 (t, 2H), 3.80 (s, 3H), 3.95 (s, 3H), 5.40 (s, 2H), 6.65 (t, 2H), 6.80 (t, 1H), 7.58 (m, 3H), 7.90 (d, 2H), 8.00 (d, 1H), 8.45 (d, 1H), 8.60 (d, 1H).

2.1.9. t-Butyl 4-{4-[4-(N-ethoxyethylamino)-4-(bis-ethoxycarbonylmethylaminoethyl)-2,5-dimethoxyphenylethylamino]-1,8-naphthalimidylmethyl} benzoate (J8)

A suspension of 0.90 g (1.38 mmol) J7, 1.23 g (4.41 mmol) M9 (see FIG. 2B) and 0.57 g (4.41 mmol) diisopropylethylamine in 5.5 ml DMF was heated at 90° C. for 20 hours under a nitrogen atmosphere (nitrogen balloon). Then 0.67 g (2.20 mmol) more M9 was added. The mixture was heated for another 18 hours. DMF was evaporated and the residue was dissolved in 50 ml CHCl$_3$ and 50 ml water. The organic phase was washed with 50 ml saturated NaCl and dried over Na$_2$SO$_4$. The solvent was evaporated to give 2.7 g brown oil.

This oil was purified on 13 g silica gel 100, using CHCl$_3$ as eluant to remove unreacted J7 and then using CHCl$_3$/ethyl acetate (4/1, v/v), wherein 0.40 g of the pure desired product (yield: 32%).

$^1$H-NMR (CDCl$_3$), δ (ppm): 1.25 (m, 9H), 1.55 (s, 9H), 2.85 (t, 2H), 3.05 (t, 2H), 3.30 (s, 3H), 3.35 (t, 2H), 3.55 (m, 6H), 3.70 (t, 2H), 3.80 (s, 3H), 3.95 (s, 3H), 5.40 (s, 2H), 6.65 (t, 2H), 6.80 (t, 1H), 7.58 (m, 3H), 7.90 (d, 2H), 8.00 (d, 1H), 8.45 (d, 1H), 8.60 (d, 1H).

FABMS (70 eV, m-nitrobenzyl alcohol dispersion with LiI): 876 (77%), (M+Li); 710 (100%), (dealkylated luminophore-ionophore).

Calcd. for C$_{42}$H$_{49}$N$_3$O$_{13}$: C 66.36; H 6.96; N 6.45; Found: C 65.68; H 7.08; N 6.35.

2.1.10. 4-{4-[4-(N-ethoxyethylamino)-4-(bis-ethoxycarbonylmethyl-aminoethyl)-2,5-dimethoxyphenylethylamino]-1,8-naphthalimidylmethyl}-benzoic acid (J9)

2 ml trifluoroacetic acid (TFA) was added to a solution of 0.40 g (0.46 mmol) J8 in 8 ml CH$_2$Cl$_2$. The resultant solution was stirred at room temperature for about 1 hour, till the TLC indicated that most of the J8 had been hydrolyzed. The mixture was diluted with 20 ml CHCl$_3$ and evaporated. The residue was dissolved in 20 ml CHCl$_3$ and evaporated again. The process was repeated two more times in order to remove the TFA completely, whereupon 0.36 g gum was obtained (yield: 95%). This was directly used for immobilization.

2.1.11. Immobilization of 4-{4-[4-(N-ethoxyethylamino)-4-(bis-ethoxycarbonylmethyl-aminoethyl)-2,5-dimethoxyphenylethylamino]-1,8-naphthalimidylmethyl } benzoic acid on aminocellulose (J10)

0.36 g (0.45 mmol) of indicator J9, 0.93 g (4.5 mmol) N,N-dicyclohexyl-1,3-carbodiimide, 0.52 g (4.5 mmol) N-hydroxysuccinimide and 10 g (~3 meq.) activated cellulose (prepared according to SU-A-1 028 677, CA 99:177723h) were suspended in 50 ml DMF for 20 hours. The cellulose fiber was filtered and washed with 5×50 ml DMF, 50 ml water, 2×50 ml 0.2 N HCl, 50 ml water, 2×50 ml 0.2 N NaOH and 10×50 ml water. The resultant fiber was ready for hydrolysis.

2.1.12. Hydrolysis of 4-{4-[4-(N-ethoxyethylamino)-4-(bis-ethoxycarbonylmethylaminoethyl)-2,5-dimethoxyphenylethylamino]- 1,8-naphthalimidylmethyl} benzoic acid immobilized on aminocellulose to free the carboxyl groups for calcium binding (J11)

The cellulose powder with immobilized indicator (J10) prepared in the previous step was suspended in 50 ml 1 N KOH. The suspension was heated to 80° C. for 5 min, stirred at room temperature for 3 hours, filtered and washed with 20×50 ml water till the filtrate became neutral. Then it was washed with 2×50 ml acetone and 2×50 ml ether and dried at room temperature for 16 hours prior to testing.

2.2. Synthesis of a luminophore-ionophore using X7* as ionophore 2.2.1. 2,5-Diethoxybenzaldehyde (N3)

A suspension of 9.66 g (70 mmol) 2,5-dihydroxybenzaldehyde N2, 32.75 g (210 mmol) iodoethane, 24.19 g (175 mmol) K$_2$CO$_3$ in 350 ml acetone was heated to reflux for 18 hours under nitrogen. The solvent was evaporated and the residue was dissolved in 300 ml CHCl$_3$ and 300 ml water. The organic phase was washed with 2×300 ml 2.5% Na$_2$CO$_3$ and 300 ml saturated NaCl and dried over Na$_2$SO$_4$. The solvent was evaporated and the residue (13.5 g) purified with a silica gel column (silica gel 100, CHCl$_3$/cyclohexane: 1/1, v/v), affording 8.61 g light yellow oil, which crystallized after cooling to room temperature (yield. 63%).

$^1$H-NMR (CDCl$_3$), δ (ppm): 1.38 (t, 3H), 1.42 (t, 3H), 4.00 (q, 2H), 4.10 (q, 2H), 6.90 (d, 1H), 7.10 (d, 1H), 7.30 (s, 1H), 10.45 (s, 1H).

2.2.2. 2,5-Diethoxy-β-nitrostyrene (N4)

A mixture of 8.35 g (43 mmol) N3, 26.24 g (430 mmol) nitromethane, 33.10 g (430 mmol) ammonium acetate in 86 ml acetic acid was warmed slowly to 80° C. and kept at this temperature for 2 hours. After cooling to room temperature, the mixture was poured into 800 ml icy water. The resultant precipitate was filtered, washed with 3×100 ml water and dried over P$_2$O$_5$ for 18 hours, wherein 8.15 g yellow prisms were obtained (yield: 80%).

$^1$H-NMR (CDCl$_3$), δ (ppm): 1.40 (t, 3H), 1.50 (t, 3H), 4.00 (q, 2H), 4.12 (q, 2H), 6.85 (d, 1H), 6.96 (m, 2H), 7.84 (d, 1H), 8.60 (d, 1H).

2.2.3. 2,5-Diethoxyphenethylamine (N5)

A solution of 8.00 g (33.7 mmol) N4 in 50 ml THF was added slowly into a suspension of 13.37 g (337 mmol) lithium aluminum hydride in 500 ml THF at boiling temperature during 1 hour. The mixture was heated to reflux for another 4 hours. The mixture was then cooled with ice-water bath to ~15° C. and quenched with 18% NaOH. The precipitate was filtered off, the filtrate evaporated to dryness and the residue dissolved in 50 ml CHCl$_3$. This solution was extracted with 2×50 ml 1 N HCl. The aqueous extracts were basified with 40% NaOH to pH>12 and then extracted with 2×50 ml CHCl$_3$ and dried over K$_2$CO$_3$. The solvent was evaporated to afford 5.80 g light yellow oil (yield: 84%).

$^1$H-NMR (CDCl$_3$), δ (ppm): 1.40 (t, 6H), 1.80 (br.s, 2H), 2.75 (t, 2H), 2.95 (t, 2H), 4.00 (q, 4H), 6.75 (m, 3H).

2.2.4. 4-Nitro-2,5-diethoxyphenethylamine (N6)

5.23 g (25 mmol) 2,5-diethoxyphenethylamine N5 was mixed with 10 ml water and cooled to 0° C. while 3 ml conc. HCl was added slowly. The resultant milky emulsion was to cooled 0 to 5° C. and 13.5 ml conc. HNO$_3$ was added slowly and carefully within about 2 hours. The temperature was kept below 10° C. The mixture solidified when about half of the HNO$_3$ had been added. 50 ml icy water was added to render the mixture stirrable. Then the rest of the HNO$_3$ was added. The mixture was warmed up to room temperature and stirred at room temperature for 3 hours, basified to pH>12 with 40% NaOH and then extracted with 2×100 ml CHCl$_3$. The CHCl$_3$ extraction was back washed with 3×100 ml 0.5 M NaOH and dried over 10 g K$_2$CO$_3$. The solvent was evaporated to afford 3.22 g orange oil (yield: 52%), which crystallized when cool.

$^1$H-NMR (CDCl$_3$), δ (ppm): 1.40 (m, 6H), 1.75 (br.s, 2H), 2.80 (t, 2H), 2.95 (t, 2H), 4.05 (q, 2H), 4.15 (q, 2H), 6.90 (s, 1H), 7.40 (s, 1H).

2.2.5. 4-Amino-2,5-diethoxyphenethylamine (N7)

3.05 g (12.0 mmol) 4-nitro-2,5-diethoxyphenethylamine N6 was dissolved in 50 ml ethanol, and 1.5 g 10% palladium on carbon black was added. This suspension was hydrogenated at 2.2 atm. for 18 hours, till no more hydrogen uptake was observed. The catalyst was filtered off and the solvent was evaporated to afford 2.75 g light yellow oil (yield: 102%).

$^1$H-NMR (CDCl$_3$), δ (ppm): 1.25 (m, 6H), 1.40 (br.t, 4H), 2.90 (t, 2H), 3.20 (t, 2H), 3.75 (q, 2H), 3.95 (m, 2H), 6.30 (s, 1H), 6.65 (s, 1H).

2.2.6. t-Butyl 4-[4-(4-amino-2,5-diethoxyphenylethylamino)-1,8-naphthalimidylmethyl]-benzoate (N8)

A suspension of 2.70 g (12.0 mmol) N7 and 1.68 g (4 mmol) C3 (see 2.1.7. and FIG. 3A) in 6 ml N-methylpyrrolidinone (NMP) was heated at 85° C. for 5 hours. The mixture was cooled and poured into 114 ml water. The resultant precipitate was filtered off, washed with 3×20 ml water and dried over P$_2$O$_5$ for 18 hours, wherein 1.9 g crude product was obtained. The crude product was purified with a silica gel column using CHCl$_3$ as eluant to afford 0.47 g pure product (yield: 19%).

$^1$H-NNR (CDCl$_3$), δ (ppm): 1.35 (t, 3H), 1.45 (t, 3H), 1.55 (s, 9H), 3.10 (t, 2H), 3.60 (t, 2H), 3.98 (q, 2H), 4.12 (q, 2H), 5.40 (s, 2H), 6.75 (m, 1H), 7.58 (m, 3H), 7.90 (d, 2H), 8.00 (d, 1H), 8.45 (d, 1H), 8.60 (d, 1H).

2.2.7. t-Butyl 4-{4-[4-(bis-ethoxycarbonylmethoxyethylamino)-2,5-diethoxyphenylethylamino]-1,8-naphthalimidylmethyl } benzoate (N9)

A suspension of 0.46 g (0.75 mmol) N8, 0.50 g (3 mmol) M25 (for synthesis see 1.7. and FIG. 2C), 0.42 g (3 mmol) K$_2$CO$_3$ and 0.25 g (1.5 mmol) KI in 5 ml DMF was heated at 83° C. for 20 hours under a nitrogen atmosphere (nitrogen balloon). Then 0.50 g (2.20 mmol) more M25 and 0.42 g more K$_2$CO$_3$ were added. The mixture was heated for another 18 hours. DMF was evaporated and the residue was dissolved in 50 ml CHCl$_3$ and 50 ml water. The organic phase was washed with 50 ml saturated NaCl and dried over Na$_2$SO$_4$. The solvent was evaporated to give 1.27 g brown oil. This oil was purified on 13 g silica gel 100, using CHCl$_3$ as eluant to remove unreacted N8 and then using CHCl$_3$/ethyl acetate (4/1, v/v). 0.23 g of the desired pure product was obtained (yield: 35%).

$^1$H-NMR (CDCl$_3$), δ (ppm): 1.25 (m, 9H), 1.55 (s, 9H), 2.85 (t, 2H), 3.05 (t, 2H), 3.30 (s, 3H), 3.35 (t, 2H), 3.55 (m, 6H), 3.70 (t, 2H), 3.80 (s, 3H), 3.95 (s, 3H), 5.40 (s, 2H), 6.65 (t, 2H), 6.80 (t, 1H), 7.58 (m, 3H), 7.90 (d, 2H), 8.00 (d, 1H), 8.45 (d, 1H), 8.60 (d, 1H).

2.2.8. 4-{4-[4-(Bis-ethoxycarbonylmethoxyethylamino)-2,5-diethoxyphenylethylamino]-1,8-naphthalimidylmethyl} benzoic acid (N10)

1 ml Trifluoroacetic acid (TFA) was added into a solution of 0.20 g (0.23 mmol) N9 in 4 ml CH$_2$Cl$_2$. The resultant solution was stirred at room temperature for about 1 hour when the TLC indicated that most of N9 was hydrolyzed. The mixture was diluted with 20 ml CHCl$_3$ and evaporated. The residue was dissolved in 20 ml CHCl$_3$ and evaporated again. The process was repeated two more times in order to remove TFA completely, whereupon 0.18 g gum was obtained (yield: 95%). This was used directly for immobilization.

2.2.9. Immobilization of 4-{4-[4-(bis-ethoxycarbonylmethoxyethylamino)-2,5-diethoxyphenylethylamino]-1,8-naphthalimidylmethyl} benzoic acid on aminocellulose (N11)

0.18 g (0.23 mmol) of N10, 0.46 g (2.3 mmol) N,N-dicyclohexyl-1,3-carbodiimide, 0.26 g (2.3 mmol) N-hydroxysuccinimide and 5 g (~1.5 meq.) activated cellulose (prepared according to SU-A-1 028 677, CA 99:177723h) were suspended in 50 ml DMF for 20 hours. The cellulose fiber was filtered and washed with 5×50 ml DMF, 50 ml water, 2×50 ml 0.2 N HCl, 50 ml water, 2×50 ml 0.2 N NaOH and 10×50 ml water. The resultant fiber was ready for hydrolysis.

2.2.10. Hydrolysis of 4-{4-[4-(Bis-ethoxycarbonylmethoxyethylamino)-2,5-diethoxyphenylethylamino]-1,8-naphthalimidylmethyl} benzoic acid immobilized on aminocellulose to free the carboxyl groups for calcium binding (N12)

The cellulose powder with immobilized indicator (N11) prepared in the previous step was suspended in 50 ml 1 N KOH. The suspension was heated to 80° C. for 5 min, stirred at room temperature for 3 hours, filtered, and the precipitate washed with 20×50 ml water, till the filtrate became neutral. Then it was washed with 2×50 ml acetone and 2×50 ml ether and dried at room temperature for 16 hours prior to testing.

3. Preparation of optical sensors (sensor discs) of the invention 0.5 g sieved (25-μm) aminocellulose fibers with immobilized indicator J11 (X3*), which had been prepared as described in Section 2.1.12, was suspended in 9.5 g 10% hydrogel D4 (Tyndale Plains-Hunter LTD. Ringoes, N.J. 08551) in 90% ethanol-water for 16 hours. The resultant homogeneous dispersion was coated onto a polyester foil (Melinex foil, ICI America) with a final dry thickness of 10 μm. This foil was overcoated with 3% carbon black in 10%

D4 hydrogel in 90% ethanol-water with a final dry thickness of 5 μm. Then a small disc 2.5 cm in diameter was punched out and soaked in buffer for at least 16 hours for activation.

The same procedure was also used for preparing sensor discs comprising immobilized indicators using X2* or X7* (=N12) as the ionophoric moiety.

Figure 4:
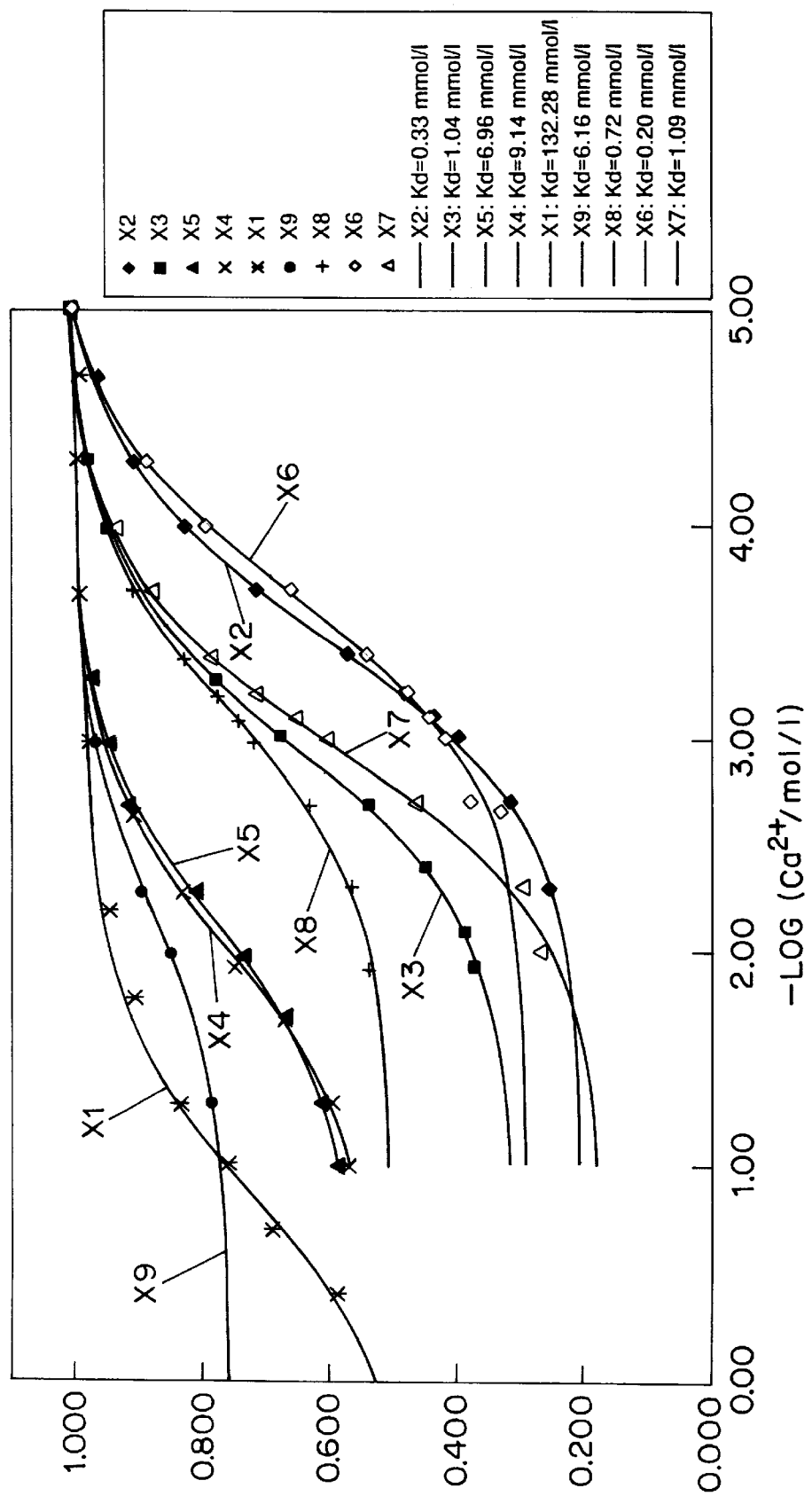
FIG. 4 is a graph of relative absorption values versus $C_a^{2+}$ concentration for ionophores in accordance with the invention.

4. Determination of the $K_d$ values of ionophores of the invention 4.1. Determination of the absorption properties of ionophores of the invention FIG. 4 shows the relative absorption values ($Ca^{2+}$ titration curves) of ionophores X1 to X9 of the invention represented in FIG. 1 in aqueous solution (30 mmol/l tris/HCl buffer; $CO_2$-free; pH 7.4) in dependence on the concentration of $Ca^{2+}$ (0.00001 to 0.5 mol/l $Ca^{2+}$) at an absorption wavelength of 248 nm.

The absorption values in dependence on the $Ca^{2+}$ concentration were measured using a commercial photometer, at an absorption wavelength of 248 nm. The resulting titration curves were normalized to the value $A_{max}=1$ at a $Ca^{2+}$ concentration of 0.00001 mol/l using Equation 4 (see below).

4.2 Determination of the $K_d$ values of the ionophores

The $K_d$ values of the ionophores were determined from the measured absorption values of the $Ca^{2+}$-titration curves according to Equation 3 (see above) and Equation 4

$$A_x = A_{max}\left(1 + \frac{Q-1}{1 - 10^{(pKd-\log(cCa))}}\right), \quad (4)$$

wherein $A_x$ is the normalized absorption value at the given $Ca^{2+}$ concentration, $A_{max}$ is the absorption value at 0.00001 mol/l $Ca^{2+}$ and $pK_d$ has the meaning indicated in Equation 3. Parameter Q allows for the fact that the absorption values at high $Ca^{2+}$ concentrations do not approach zero.

The $K_d$ values for ionophores X1 to X9 of the invention are given in Table 1. They were determined from the found $pK_d$ values by means of Equation 3.

TABLE 1

| Ionophore | $K_d$ (mol/l) | Group[1] |
|---|---|---|
| X1 | 0.123 | I |
| X2 | 0.00033 | I |
| X3 | 0.00104 | I |
| X4 | 0.00914 | I |
| X5 | 0.00696 | I |
| X6 | 0.00020 | II |
| X7 | 0.00109 | II |
| X8 | 0.00072 | II |
| X9 | 0.00616 | III |

[1]Ionophores of Group I have a group of the general Formula II.
Ionophores of Group II have a group of the general Formula III.
Ionophores of Group III have a group of the general Formula IV.

Group I:

In the ionophores of the invention of Group I, the imino-N,N-diacetate ligands are bound to the nitrogen atom of the o-alkoxyaniline by means of a —$CH_2$—CY— group (Y=$H_2$ or O).

By a suitable choice of the substituents $R_1$ on the nitrogen atom and/or $R_2$ on the oxygen atom and/or $R_3$ on the aromatic ring of the o-anisidine, the $K_d$ value of the ionophore can be adjusted. For ionophores with Y=$H_2$, for example $K_d$ values of 0.1–10 mmol/l can be adjusted (see Table 1: X2 to X5). Compounds with Y=O are suitable for the determination of particularly high $Ca^{2+}$ concentrations (>10 mmol/l) (see Table 1: X1).

Suitable substituents $R_1$ are for example methoxyethyl (X1 and X2), ethoxyethyl (X3), phenoxyethyl (X5) or n-butyl (X4). Suitable substituents $R_2$ are for example methyl (X2 to X5), ethyl or propyl. Suitable substituents $R_3$ on the aromatic ring are electron-withdrawing or electron-donating (for example H, X1 to X5) groups.

Group II:

The ionophores of the invention of Group II have alkyloxyacetate groups (—$(CH_2)_n$—O—$CH_2$—COOH) in the ligand portion, which are bound to the nitrogen atom of the o-alkoxyaniline. n is preferably 2, for example in compounds X6 to X8. As in the ionophores of Group I, the $K_d$ values can be adjusted by varying the substituents $R_4$ on the oxygen atom (cf. for example the $K_d$ values for X6 and X7 in Table 1) and/or by inserting electron-withdrawing or electron-donating groups $R_5$ on the aromatic ring of the o-alkoxyaniline.

Suitable substituents $R_4$ are for example methyl (X6 and X8) or ethyl (X7). A suitable electron-donating group is for example H (X6, X7), a suitable electron-withdrawing group $R_5$ is for example Cl (X8).

Group III:

In the ionophores of the invention of Group III, the imino-N,N-diacetate ligand portion is bound by means of a —$CH_2$—$CH_2$— group on the oxygen atom of the o-alkoxyaniline. The nitrogen atom carries two alkoxyethyl or phenoxyethyl groups. Also in this group of compounds the $K_d$ values are adjustable by varying the residues. A suitable substituent $R_6$ is for example methyl (X9). Suitable substituents $R_7$ are electron-withdrawing or electron-donating (for example H in X9) groups.

5. Determination of the luminescence properties of luminophore-ionophores of the invention In order to measure the luminescence intensity of some compounds of the invention (luminophore-ionophores), sensor discs prepared according to the process described above (see Section 3.) were introduced into a light-transmitting thermostatted measuring cell and brought into contact with samples P (see FIG. 5) exhibiting different concentrations of $Ca^{2+}$ and different pH values.

Figure 5:
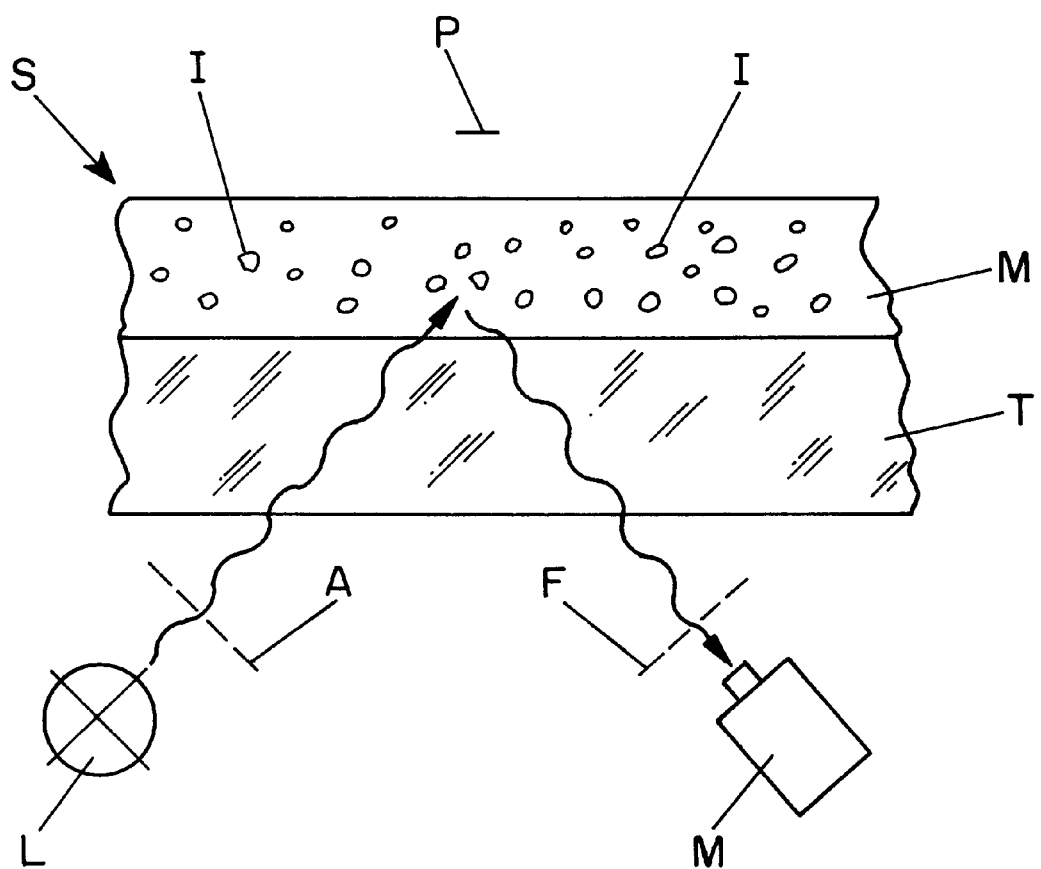
FIG. 5 is a schematic illustration of a measuring arrangement including sensor discs prepared in accordance with the invention.

The measuring arrangement is represented schematically in FIG. 5, with a portion of the sensor disc being denoted by S. The compound of the invention suspended in the hydrophilic ion-permeable polymer (hydrogel) and immobilized on aminocellulose is denoted by I. This layer M is carried by a substrate T permeable to excitation and measuring radiation, which is a transparent foil.

The optical measuring system consisted of a blue LED as the light source L, a photodiode M as the detector, optical filters A and F for selecting the wavelengths, a fiber-optic arrangement for conducting the excitation light into the polymer layer M and for conducting the emission light to the photodetector M as well as a device for electromagnetic signal processing (not illustrated). At the excitation end there was utilized an interference filter peak transmission at 480 nm) and at the emission end a 520 nmu cut-off filter.

Figure 6:
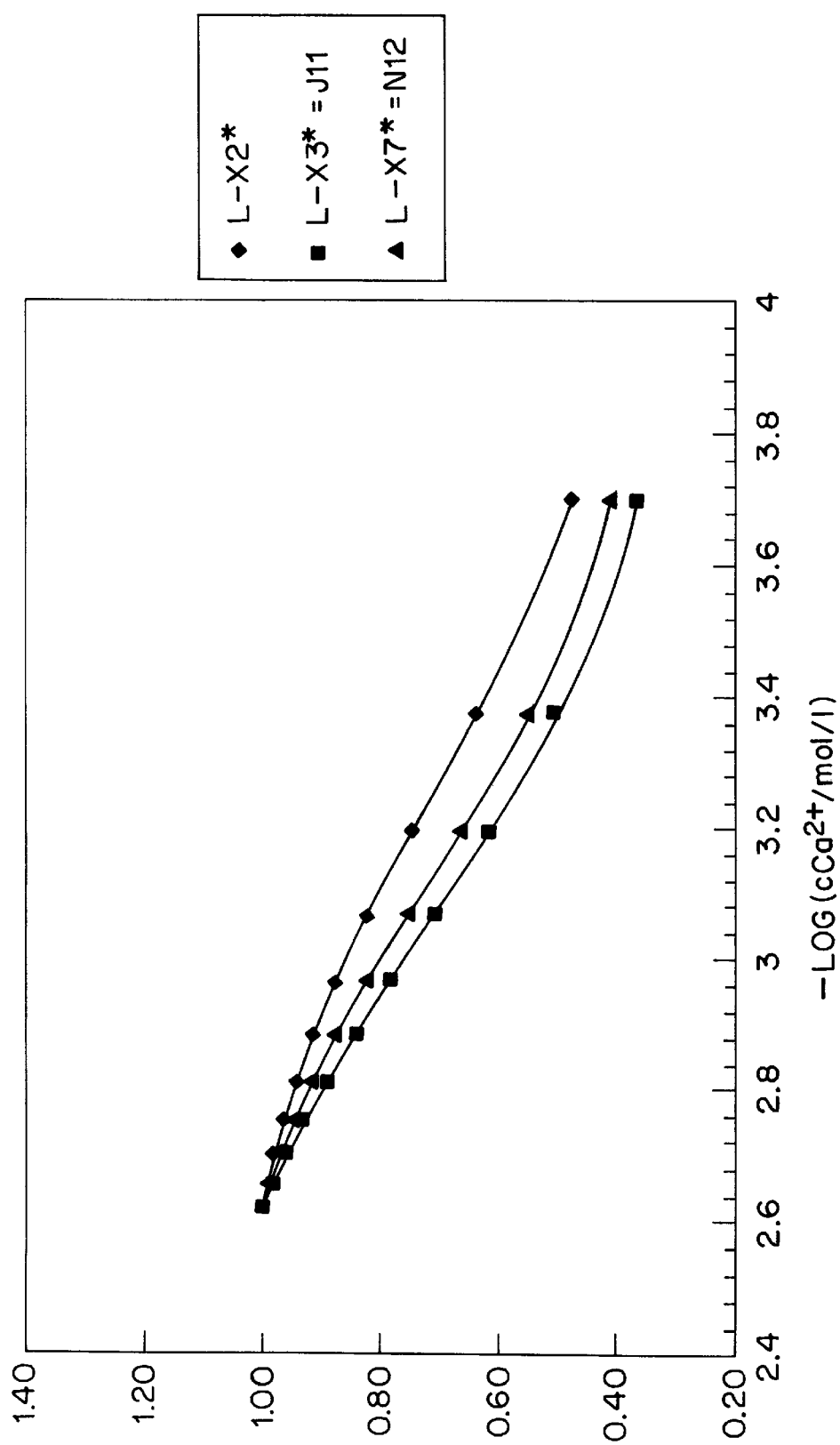
FIG. 6 is a graph of relative luminescence intensity versus negative common logarithm of calcium concentration for three luminophore-ionophore immobilized on amiriocellulose in accordance with the invention.
Figure 7:
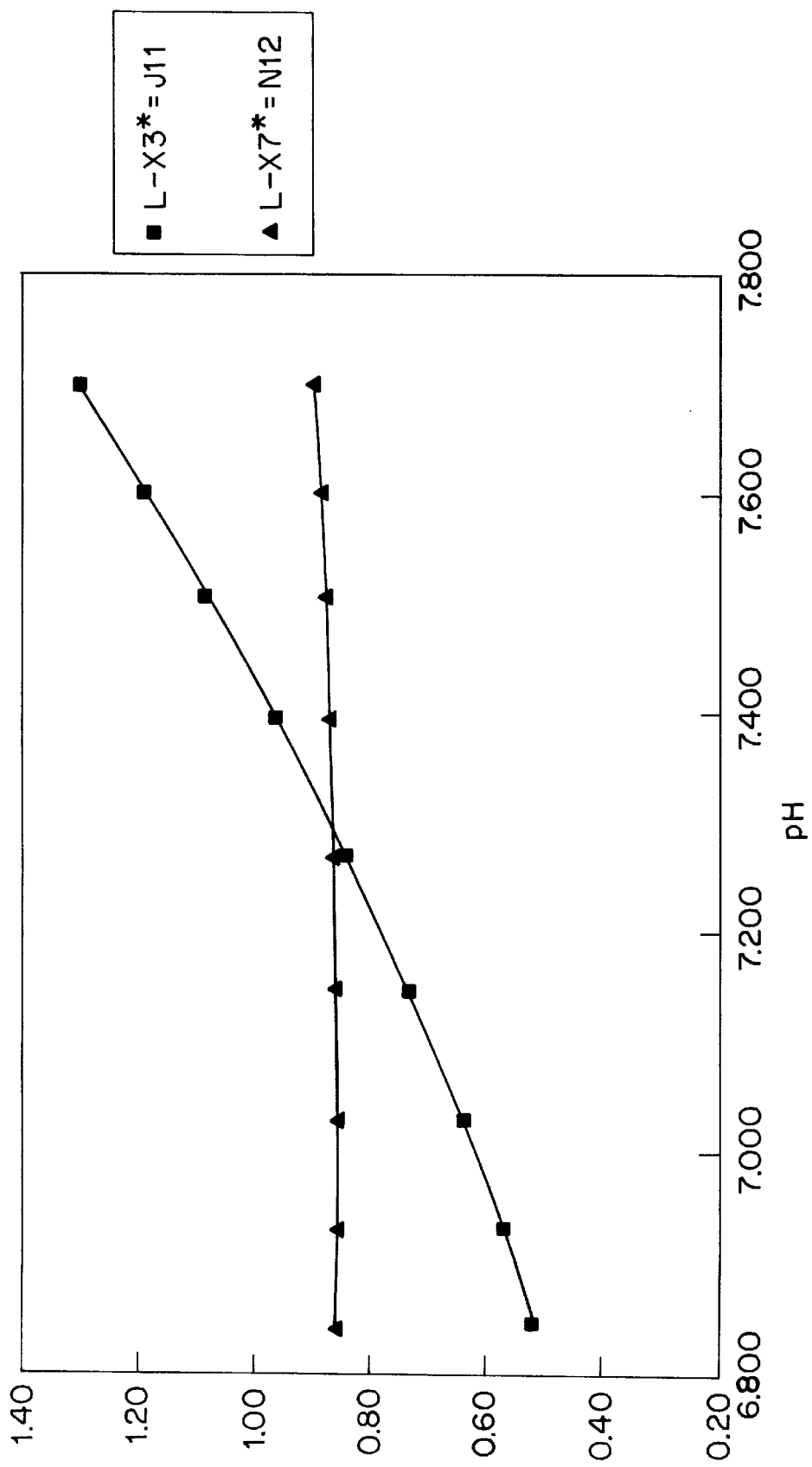
FIG. 7 is a graph of relative luminescence intensity versus pH for two luminophore-ionophores according to the invention.

FIGS. 6 and 7 show the luminescence properties of some compounds of the invention, immobilized on cellulose, as a function of the concentration of $Ca^{2+}$ and of the pH, respectively. In each Figure, the ordinates of the illustrated diagrams give the relative luminescence intensities.

FIG. 6:

FIG. 6 shows the relative luminescence intensity of three luminophore-ionophores of the invention (L-X2*, L-X3*=J11, L-X7*=N12), immobilized on aminocellulose, as a function of the negative common logarithm of the calcium concentration (0.0002, 0.0004, 0.0006, 0.0009, 0.0011, 0.0013, 0.0015, 0.0017, 0.0020, 0.0022, 0.0024 mol/l).

The measuring media that were used were 0.1 M HEPES buffers, $CO_2$-free, pH 7.4 (37° C.), with different concentrations of $CaCl_2$.

FIG. 7:

FIG. 7 shows the relative luminescence intensity of two luminophore-ionophores of the invention (L-X3*=J11, L-X7*=N12), immobilized on aminocellulose, as a function of the pH (6.841, 6.932, 7.030, 7.149, 7.271, 7.396, 7.507, 7.603, 7.700).

The measuring media that were used were 0.1 M HEPES buffers with different concentrations of HEPES acid and HEPES-Na salt and a concentration of $CaCl_2$ of 0.0013 mol/l.

As can be seen from FIG. 7, ionophores or luminophore-ionophores of the invention having an ethyl-imino-N,N-diacetate ligand portion (Group 1, $Y=H_2$) which is bound to the nitrogen of the o-anisidine show pH-dependence at physiological pH values. They are thus suitable for those measuring situations where the pH of the sample is known or can be adjusted to a known value (e.g. by pH buffers).

Further it can be seen from FIG. 7 that ionophores or luminophore-ionophores of the invention having a diethoxy-acetate ligand portion bound to the nitrogen of the o-anisidine in view of their non-significant pH-dependence in the physiological pH measuring range are particularly suited for determining $Ca^{2+}$ at a physiological pH.

What is claimed is:

1. Compound selected from the group consisting of a compound having the general Formula I:

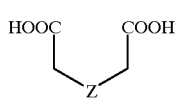

and salts thereof, wherein Z is selected from the group consisting of a group having the general Formula II:

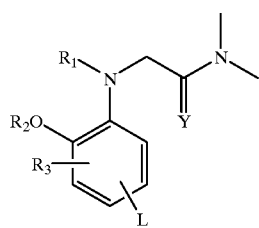

wherein $R_1$ is selected from the group consisting of alkyl having 1–4 C atoms, alkoxyalkyl with 2–5 C atoms and aryloxyalkyl whose alkyl group has 1–4 C atoms, $R_2$ is selected from the group consisting of alkyl having 1–4 C atoms and alkoxyalkyl having 2–5 C atoms, $R_3$ is selected from the group consisting of H, alkoxy having 1–4 C atoms, halogen, NO and $NO_2$, Y is selected from the group consisting of $H_2$ and O and L is a luminophoric moiety in a position para or meta to the nitrogen, a group having the general Formula III:

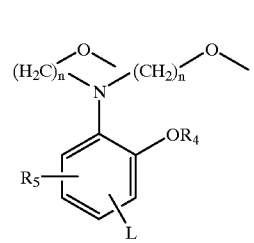

wherein n is selected from the group of 2 and 3, $R_4$ is selected from the group consisting of alkyl having 1–4 C atoms and alkoxyalkyl having 2–5 C atoms, $R_5$ is selected from the group consisting of H, alkoxy having 1–4 C atoms, halogen, NO and $NO_2$ and L is a luminophoric moiety in a position para or meta to the nitrogen, and a group having the Formula IV:

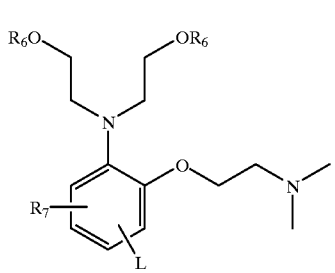

wherein $R_6$ is selected from the group consisting of alkyl having 1–3 C atoms and phenyl, $R_7$ is selected from the group consisting of H, alkoxy having 1–4 C atoms, halogen, NO and $NO_2$ and L is a luminophoric moiety in a position para or meta to the nitrogen.

2. Compound according to claim 1 having a group having the general Formula (II), $R_1$ is selected from the group consisting of alkyl having 4 C atoms, alkoxyalkyl having 3–4 C atoms and aryloxyalkyl whose alkyl group has 2 C atoms.

3. Compound according to any one of claim 1 or claim 2 having a group having, the general Formula (II), wherein $R_2$ is alkyl having 1–4 C atoms.

4. Compound according to claim 3 wherein $R_2$ is methyl.

5. Compound according to claim 4 having a group having the general Formula (II) wherein $R_3$ is located in a position para to the oxygen of an o-anisidine.

6. Compound according to claim 4 having a group having the general Formula (II) wherein $R_3$ is selected from the group consisting of H and methoxy.

7. Compound according to claim 4 having a group having the general Formula (III) wherein $R_4$ is alkyl having 1–2 C atoms.

8. Compound according to claim 4 having a group having the general Formula (III) wherein $R_5$ is located in a position para to the oxygen of an o-anisidine.

9. Compound according to claim 4 having a group having the general Formula (III) wherein $R_5$ is selected from the group consisting of H, ethoxy and Cl.

10. Compound according to claim 3 having a group having the general Formula (II) wherein $R_3$ is located in a position para to the oxygen of an o-anisidine.

11. Compound according to claim 3 having a group having the general Fomula (II) wherein $R_3$ is selected from the group consisting of H and methoxy.

12. Compound according to claim 3 having a group having the general Formula (III) wherein $R_4$ is alkyl having 1–2 C atoms.

13. Compound according to claim 3 having a group having the general Formula (III) wherein $R_5$ is located in a position para to the oxygen of an o-anisidine.

14. Compound according to claim 3 having a group having the general Formula (III) wherein $R_5$ is selected from the group consisting of H, ethoxy and Cl.

15. Compound according to any one of claim 1 or claim 2 having a group having the general Formula (II), wherein $R_3$ is located in a position para to the oxygen of an o-anisidine.

16. Compound according to claim 15 having a group having the general Formula (II) wherein $R_3$ is selected from the group consisting of H and methoxy.

17. Compound according to claim 15 having a group having the general Formula (III) wherein $R_4$ is alkyl having 1–2 C atoms.

18. Compound according to claim 15 having a group having the general Formula (III) wherein $R_5$ is located in a position para to the oxygen of an o-anisidine.

19. Compound according to claim 18 having a group having the general Formula (III) wherein $R_{15}$ is selected from the group consisting of H, ethoxy and Cl.

20. Compound according to any one of claim 1 or claim 2 having a group having the general Formula (II), wherein $R_3$ is selected from the group consisting of H and methoxy.

21. Compound according to claim 20 having a group having the general Formula (III) wherein $R_4$ is alkyl having 1–2 C atoms.

22. Compound according to claim 20 having a group having the general Formula (III) wherein $R_5$ is located in a position para to the oxygen of an o-anisidine.

23. Compound according to claim 20 having a group having the general Formula (III) wherein $R_5$ is selected from the group consisting of H, ethoxy and Cl.

24. Compound according to claim 1 having a group having the general Formula (III), wherein n=2.

25. Compound according to any one of claim 1, claim 2 or claim 24 having a group having the general Formula (III), wherein $R_4$ is alkyl having 1–2 C atoms.

26. Compound according to claim 25 having a group having the general Formula (III) wherein $R_5$ is located in a position para to the oxygen of an o-anisidine.

27. Compound according to claim 25 having a group having the general Formula (III) wherein $R_{15}$ is selected from the group consisting of H, ethoxy and Cl.

28. Compound according to any one of claim 1, claim 2 or claim 24 having a group having the general Formula (III) wherein $R_5$ is located in a position para to the oxygen of an o-anisidine.

29. Compound according to claim 28 having a group having the general Formula (III) wherein $R_5$ is selected from the group consisting of H, ethoxy and Cl.

30. Compound according to any one of claim 1, claim 2 or claim 24 having a group having the general Formula (III) wherein $R_5$ is selected from the group consisting of H, ethoxy and Cl.

31. Compound according to claim 1 having a group having the general Formula (IV) wherein $R_6$ is methyl.

32. Compound according to any one of claim 1 or claim 3 having, a group having the general Formula (IV) wherein $R_7$ is located in a position para to the oxygen of an o-anisidine.

33. Compound according to claim 32 having a group having the general Formula (IV) wherein $R_7$ is H.

34. Compound according to any one of claim 1 or claim 31 having a group having the general Formula (IV) wherein $R_7$ is H.

35. Compound according to any one of claim 1, claim 2, claim 24 or claim 31 wherein L is located in a position para to the nitrogen.

36. Compound according to any one of claim 1, claim 2, claim 24 or claim 31 wherein the compound is present in the form of the dipotassium salt.

37. Optical sensor for determining calcium ions in a sample, which sensor has a matrix comprising a compound having a luminophoric moiety and an ionophoric moiety, wherein the compound is a compound according to any one of claim 1, claim 2, claim 24 or claim 31.

38. Method for determining calcium ions in a sample comprising: providing a compound according to any one of claim 1, claim 2, claim 24 or claim 31 having a luminophoric moiety and an ionophoric moiety contacting the sample at least indirectly with the compound having a luminophoric moiety and an ionophoric moiety, wherein the ioniophoric moiety reacts with the calcium ions present in the sample, and wherein the luminophoric moiety changes its luminescence properties, measuring luminescence and determining the amount of calcium ions in the sample using the measured luminescence.

* * * * *

UNITED STATES PATENT AND TRADEMARK OFFICE
CERTIFICATE OF CORRECTION

PATENT NO. : 6,171,866 B1
DATED : January 9, 2001
INVENTOR(S) : Huarui et al.

It is certified that error appears in the above-identified patent and that said Letters Patent is hereby corrected as shown below:

Column 1,
Line 43, "PK$_d$" should read -- pK$_d$ --
Equation (3), "PK$_d$" should read -- pK$_d$ --

Column 2,
Line 23, "f.i" (unknown abbr.) should read -- e.g., --

Column 4,
Line 23, "2or" should read -- 2 or --

Column 7,
Line 11, "5-dimetlioxyphenethylamine" should read -- 5-dimethoxyphenethylamine --
Line 21, "amiriocellu-" should read -- aminocellu- --

Column 9,
Line 10, "hour The" should read -- hours. The --
Line 17, "$^1$H-NNIR" should read -- $^1$H-NMR --
Line 22, "As" should read -- A --
Line 56, "aninoethyl" should read -- aminoethyl --
Line 67, "$^1$H-NMR" should read -- ¶$^1$H-NMR --

Column 11,
Line 64, "11" (eleven) should read -- 1l -- (one liter)
Line 66, "fuirther" should read -- further --

Column 12,
Line 39, "phenitidene" should read -- phenetidene --

Column 14,
Line 22, "(s, 3H1)" should read -- (s, 3H) --
Line 32, "H-NMR" should read -- ¶H-NMR --
Line 34, "(s, 31H)" should read -- (s, 3H) --
Line 63, "-naphthalimidylrnethylbenzoic" should read -- -naphthalimidylmethylbenzoic --

Column 15,
Line 6, "-naphthalimidyknethylbenzoate" should read -- -naphthalimidylmethlbenzoate --
Line 57, "product" should read -- product was obtained --

UNITED STATES PATENT AND TRADEMARK OFFICE
CERTIFICATE OF CORRECTION

PATENT NO. : 6,171,866 B1
DATED : January 9, 2001
INVENTOR(S) : Huarui et al.

It is certified that error appears in the above-identified patent and that said Letters Patent is hereby corrected as shown below:

Column 17,
Line 60, "$^1$H-NNR" should read -- $^1$H-NMR --

Column 20,
Line 52, "nmu" should read -- nm --

Column 22,
Line 43, "$R_1$" should read -- wherein $R_1$ --
Line 48, "having," should read -- having --

Column 23,
Line 2, "Fomula" should read -- Formula --
Line 26, "claim 18" should read -- claim 15 --
Line 27, "$R_{15}$" should read -- $R_5$ --

Column 24,
Line 17, "3" should read -- 31 --
Line 41, "ioniophoric" should read -- ionophoric --

Signed and Sealed this

Fifteenth Day of January, 2002

Attest:

JAMES E. ROGAN
*Director of the United States Patent and Trademark Office*

*Attesting Officer*